US009107603B2

(12) United States Patent
 Kaku

(10) Patent No.: US 9,107,603 B2
(45) Date of Patent: Aug. 18, 2015

(54) ELECTRONIC ENDOSCOPE SYSTEM INCLUDING A SUPPRESSION SECTION

(75) Inventor: Toshihiko Kaku, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 157 days.

(21) Appl. No.: 13/336,931

(22) Filed: Dec. 23, 2011

(65) Prior Publication Data

US 2012/0197077 A1    Aug. 2, 2012

(30) Foreign Application Priority Data

Jan. 27, 2011    (JP) .................................. 2011-014725

(51) Int. Cl.
| | |
|---|---|
| *A61B 1/045* | (2006.01) |
| *A61B 1/06* | (2006.01) |
| *A61B 1/00* | (2006.01) |
| *A61B 1/05* | (2006.01) |
| *A61B 5/00* | (2006.01) |

(52) U.S. Cl.
 CPC ........... *A61B 1/0638* (2013.01); *A61B 1/00009* (2013.01); *A61B 1/00186* (2013.01); *A61B 1/05* (2013.01); *A61B 1/0653* (2013.01); *A61B 1/0669* (2013.01); *A61B 5/0059* (2013.01); *A61B 1/063* (2013.01); *A61B 1/0646* (2013.01); *A61B 5/7232* (2013.01)

(58) Field of Classification Search
 CPC ........... A61B 1/00009; A61B 1/00186; A61B 1/10638; A61B 1/0646; A61B 1/0653; A61B 1/0669; A61B 5/0059

USPC .......... 600/178, 180, 109, 118, 160, 476, 477
 See application file for complete search history.

(56) References Cited

U.S. PATENT DOCUMENTS

| 4,885,634 | A | * | 12/1989 | Yabe .............................. 348/71 |
| 7,678,045 | B2 | * | 3/2010 | Igarashi ........................ 600/160 |
| 8,000,776 | B2 | * | 8/2011 | Gono ............................. 600/476 |
| 2002/0062061 | A1 | * | 5/2002 | Kaneko et al. ................ 600/118 |

(Continued)

FOREIGN PATENT DOCUMENTS

| JP | 2000-148987 A | 5/2000 |
| JP | 2002-034893 A | 2/2002 |

(Continued)

OTHER PUBLICATIONS

European Search Report dated Jun. 6, 2012.

(Continued)

*Primary Examiner* — John P Leubecker
(74) *Attorney, Agent, or Firm* — McGinn IP Law Group, Pllc

(57) ABSTRACT

An electronic endoscope system includes a light source apparatus, a CCD, and a processor apparatus. The light source apparatus applies illumination light to a target portion. The target portion includes a surface blood vessel and a subsurface blood vessel. The CCD captures light reflected from the target portion. The processor apparatus generates an image based on an imaging signal from the CCD. The processor apparatus has a suppression processor. Out of the surface blood vessel and the subsurface blood vessel in an image, the suppression processor reduces contrast of a non-target blood vessel relative to that of a target blood vessel to suppress or reduce display of the non-target blood vessel relative to that of the target blood vessel.

7 Claims, 21 Drawing Sheets

(56) References Cited

U.S. PATENT DOCUMENTS

| | | |
|---|---|---|
| 2003/0139650 A1* | 7/2003 | Homma .................. 600/181 |
| 2003/0176768 A1* | 9/2003 | Gono et al. ............. 600/109 |
| 2007/0149854 A1* | 6/2007 | Igarashi ................. 600/167 |
| 2007/0263929 A1* | 11/2007 | Kaji ....................... 382/168 |
| 2008/0021272 A1* | 1/2008 | Doguchi et al. ........ 600/109 |
| 2008/0194972 A1* | 8/2008 | Gono ...................... 600/476 |
| 2009/0012361 A1* | 1/2009 | MacKinnon et al. ... 600/118 |
| 2009/0040298 A1* | 2/2009 | Yamazaki et al. ....... 348/68 |
| 2009/0058999 A1 | 3/2009 | Gono et al. |
| 2009/0091614 A1* | 4/2009 | Gono et al. .............. 348/68 |
| 2009/0149706 A1* | 6/2009 | Yamazaki et al. ....... 600/109 |
| 2009/0167149 A1* | 7/2009 | Ito .......................... 313/501 |
| 2011/0077462 A1* | 3/2011 | Saitou et al. ............ 600/109 |
| 2011/0112362 A1* | 5/2011 | Minetoma ............... 600/109 |
| 2011/0237894 A1* | 9/2011 | Ozawa et al. ........... 600/168 |
| 2011/0257484 A1* | 10/2011 | Mizuyoshi et al. ...... 600/178 |
| 2012/0179050 A1* | 7/2012 | Saito ....................... 600/476 |

FOREIGN PATENT DOCUMENTS

| | | |
|---|---|---|
| JP | 2005-323758 A | 11/2005 |
| JP | 2006-061620 A | 3/2006 |
| JP | 2006-341075 A | 12/2006 |
| JP | 2007-264537 A | 10/2007 |
| JP | 2011-010998 A | 1/2011 |
| WO | WO 2007/099681 A1 | 9/2007 |

OTHER PUBLICATIONS

Notification of Reasons for Refusal dated Nov. 30, 2012, with English translation.

Notification of Reasons for Refusal dated Apr. 23, 2014, with English translation.

English Translation of Japanese Office Action drafted Sep. 29, 2014.

* cited by examiner

ELECTRONIC ENDOSCOPE SYSTEM INCLUDING A SUPPRESSION SECTION

BACKGROUND OF THE INVENTION

1. Field of the Invention

The present invention relates to an electronic endoscope system for capturing an image of a portion to be observed in a subject using an electronic endoscope.

2. Description Related to the Prior Art

Diagnoses and treatments using an electronic endoscope are common in the medical field. In an electronic endoscope system for capturing an image of a portion to be observed in a subject using an electronic endoscope, normal light observation using white light (hereinafter referred to as the normal light) as illumination light is performed. However, it is often difficult to observe details of tissue under the normal light observation. To observe the details, special light observation has been performed recently. Under the special light observation, an image is captured while narrowband light (hereinafter referred to as the special light) in a specific wavelength range is applied to the portion to be observed. Thereby, it becomes easy to observe details of specific tissue in the image captured. Under the special light observation, an image shows clear contrast between tissue which absorbs the special light and remaining tissue. Thus, the tissue which absorbs the special light is enhanced in the image.

On the other hand, a technique to improve contrast of specific tissue by applying image processing to an image has been known. Thereby, the specific tissue is enhanced in the image. For example, by applying frequency enhancement processing for enhancing an image of a predetermined frequency, contrast of a blood vessel (hereinafter referred to as the surface blood vessel) located in a mucosal surface or a blood vessel (hereinafter referred to as the subsurface blood vessel) located below the surface blood vessel improves (see Japanese Patent Laid-Open Publication No. 2000-148987).

Under the special light observation, the tissue which absorbs the special light is enhanced. However, remaining tissue observable under the normal light observation is also shown in the image in the same manner as the normal light observation. Accordingly, the tissue which absorbs the special light is superposed on the remaining tissue observable under the normal light observation in the image displayed.

For example, under the normal light observation, a surface blood vessel is superposed on a subsurface blood vessel in an image. When the special light observation is performed, the image of the surface blood vessel, which absorbs the special light, is enhanced in a state that the surface blood vessel is superposed on the subsurface blood vessel. The subsurface blood vessel often hinders the close observation of the surface blood vessel.

Conversely, when the special light observation is performed using special light absorbed by the subsurface blood vessel to enhance the subsurface blood vessel, the subsurface blood vessel is enhanced while being superposed by the surface blood vessel. The surface blood vessel often hinders the close observation of the subsurface blood vessel.

On the other hand, frequency enhancement processing improves contrast of an image of a predetermined frequency. The frequency enhancement processing is applied to an image captured under the special light observation. However, tissue under observation may be enhanced incorrectly depending on a subject distance.

More specifically, when the subject distance is long, a subsurface blood vessel is narrow in an image captured. Accordingly, the frequency enhancement processing, aiming at the surface blood vessel, enhances the subsurface blood vessel instead. Conversely, when the subject distance is short, the surface blood vessel is wide in the image. Accordingly, frequency enhancement processing, aiming at the subsurface blood vessel, enhances the surface blood vessel instead.

Under the special light observation, the surface blood vessel is superposed on the subsurface blood vessel in an image. It is difficult to observe a target blood vessel when a non-target blood vessel is enhanced with the frequency enhancement processing.

To solve the problem, it is desired to improve visibility of the target blood vessel without being hindered by non-target blood vessel(s).

SUMMARY OF THE INVENTION

An object of the present invention is to improve visibility of a target blood vessel without being hindered by non-target blood vessel(s).

The electronic endoscope system of the present invention includes an illumination section, an imaging section, an image generating section, and a suppression section. The illumination section applies illumination light to a portion to be observed inside a body. The portion includes a surface blood vessel and a subsurface blood vessel located deeper than the surface blood vessel. One of the surface blood vessel and the subsurface blood vessel is a target blood vessel to be observed. The illumination light includes first illumination light and second illumination light. Light absorption by the target blood vessel is relatively large in a wavelength range of the first illumination light. Light absorption by a non-target blood vessel is relatively large in a wavelength range of the second illumination light. The imaging section captures reflection light reflected from the portion to output at least a first imaging signal and a second imaging signal. The first imaging signal corresponds to the first illumination light. The second illumination signal corresponds to the second imaging light. The image generating section generates an image based on the at least first and second imaging signals. The suppression section reduces contrast of the non-target blood vessel in the image to reduce display of the non-target blood vessel relative to that of the target blood vessel.

It is preferable that the imaging section is a color image sensor. The color image sensor has at least a first color filter of a first color and a second color filter of a second color on each pixel. The first color filter corresponds to the wavelength range of the first illumination light. The second color filter corresponds to the wavelength range of the second illumination light. The color image sensor outputs a first color signal being the first imaging signal and a second color signal being the second imaging signal.

It is preferable that the imaging section outputs a third color signal in addition to the first and second color signals. Contrast of the non-target blood vessel is low in the third color signal. The suppression section reduces the contrast of the non-target blood vessel by adding the third color signal to the second color signal.

It is preferable that the suppression section changes an addition rate of the third color signal to change a degree of reducing display of the non-target blood vessel.

It is preferable that the target blood vessel is the surface blood vessel. The non-target blood vessel is the subsurface blood vessel.

It is preferable that the color image sensor outputs B, G, and R signals corresponding to respective first to third color signals. The image generating section uses the B signal for blue and green pixels in the image, the G signal for a red pixel in the image, and a sum of the R signal and the G signal for the red pixel to generate the image.

It is preferable that the suppression section controls a spectrum of the illumination light to reduce the contrast of the non-target blood vessel.

It is preferable that the suppression section makes a light quantity of the second illumination light from the illumination section relatively small to reduce the contrast.

It is preferable that the target blood vessel is the subsurface blood vessel, and the non-target blood vessel is the surface blood vessel.

It is preferable that the illumination section has first and second light sources and a phosphor. Each of the first and second light sources emits light having a wavelength range of the first illumination light. The phosphor absorbs a part of the light emitted from the first and second light sources. The phosphor is excited by absorbed light to emit fluorescence. The fluorescence has a wavelength range of the second illumination light. The phosphor allows remaining light to pass therethrough. The light emitted from the first and second light sources and the fluorescence form white light. Fluorescence excitation efficiency of the second light source is higher than that of the first light source. The suppression section increases a proportion of the light quantity of the second light source relative to that of the first light source to increase a light quantity of the fluorescence generated by the light from the second light source so as to make the light quantity of the first illumination light relatively small.

It is preferable that the illumination section adds light to the illumination light to control the spectrum. The light being added has a wavelength range to reduce the contrast of the non-target blood vessel.

It is preferable that the suppression section has a first suppression section and a second suppression section. The first suppression section adds the third color signal to the second color signal to reduce the contrast of the non-target blood vessel. The second suppression section controls a spectrum of the illumination light to reduce the contrast of the non-target blood vessel. It is preferable that the electronic endoscope system further includes a selection section for functioning one of the first and second suppression sections in accordance with the target blood vessel or the non-target blood vessel.

It is preferable that the electronic endoscope system further includes an enhancement processing section for performing enhancement processing to enhance the target blood vessel relative to the non-target blood vessel.

It is preferable that the suppression section reduces the display of the non-target blood vessel in conjunction with the enhancement processing performed by the enhancement processing section.

It is preferable that the electronic endoscope system further includes a color tone corrector for correcting a color tone of the image.

According to the present invention, the visibility of a target blood vessel is improved without being hindered by remaining tissue including non-target blood vessels.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
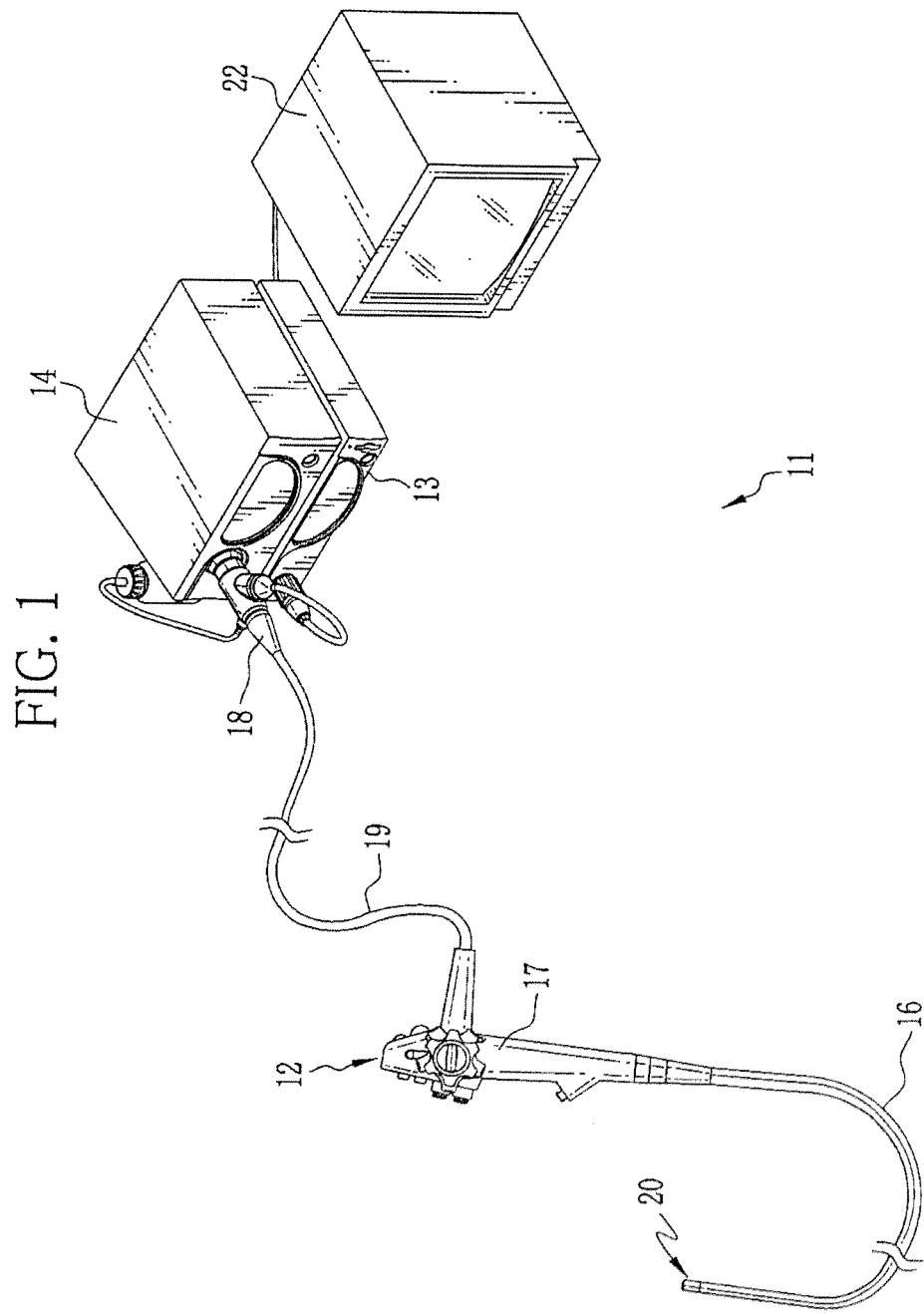
FIG. 1 is an explanatory view showing a configuration of an electronic endoscope system.

As shown in FIG. 1, an electronic endoscope system 11 is provided with an electronic endoscope 12, a processor apparatus 13, and a light source apparatus 14. The electronic endoscope 12 has a flexible insert section 16, a handling section 17, a connector 18, and a universal cord 19. The insert section 16 is inserted into a body of a subject. The handling section 17 is connected to a base portion of the insert section 16. The connector 18 connects the processor apparatus 13 and the light source apparatus 14. The universal cord 19 connects between the handling section 17 and the connector 18. A CCD image sensor (see FIG. 2, hereinafter referred to as the CCD) 21 is provided at a distal end (hereinafter, the distal portion) 20 of the insert section 16. The CCD 21 captures an image of living tissue (hereinafter referred to as the target portion) inside the body of the subject.

The handling section 17 is provided with operation members. The operation members include an angle knob, an air/water button, a release button, a zoom button, and a selection button. The angle knob is used for bending the distal portion 20 in horizontal and vertical directions. The air/water button is used for injecting air or water from a tip of the insert section 16. The release button is used for still-recording an observation image. The zoom button is used for enlarging or reducing the observation image displayed on a monitor 22. The selection button is used for selecting the normal light observation or the special light observation.

The processor apparatus 13 is electrically connected to the light source apparatus 14. The processor apparatus 13 controls the entire electronic endoscope system 11. The processor apparatus 13 supplies power to the electronic endoscope 12 through a transmission cable (not shown) inserted through the universal cord 19 and the insert section 16. The processor apparatus 13 controls the operation of the CCD 21. The processor apparatus 13 obtains an imaging signal, outputted from the CCD 21 through the transmission cable, and performs various image processes to the imaging signal to generate image data. The image data is displayed as an observation image on the monitor 22 cable-connected to the processor apparatus 13.

Figure 2:
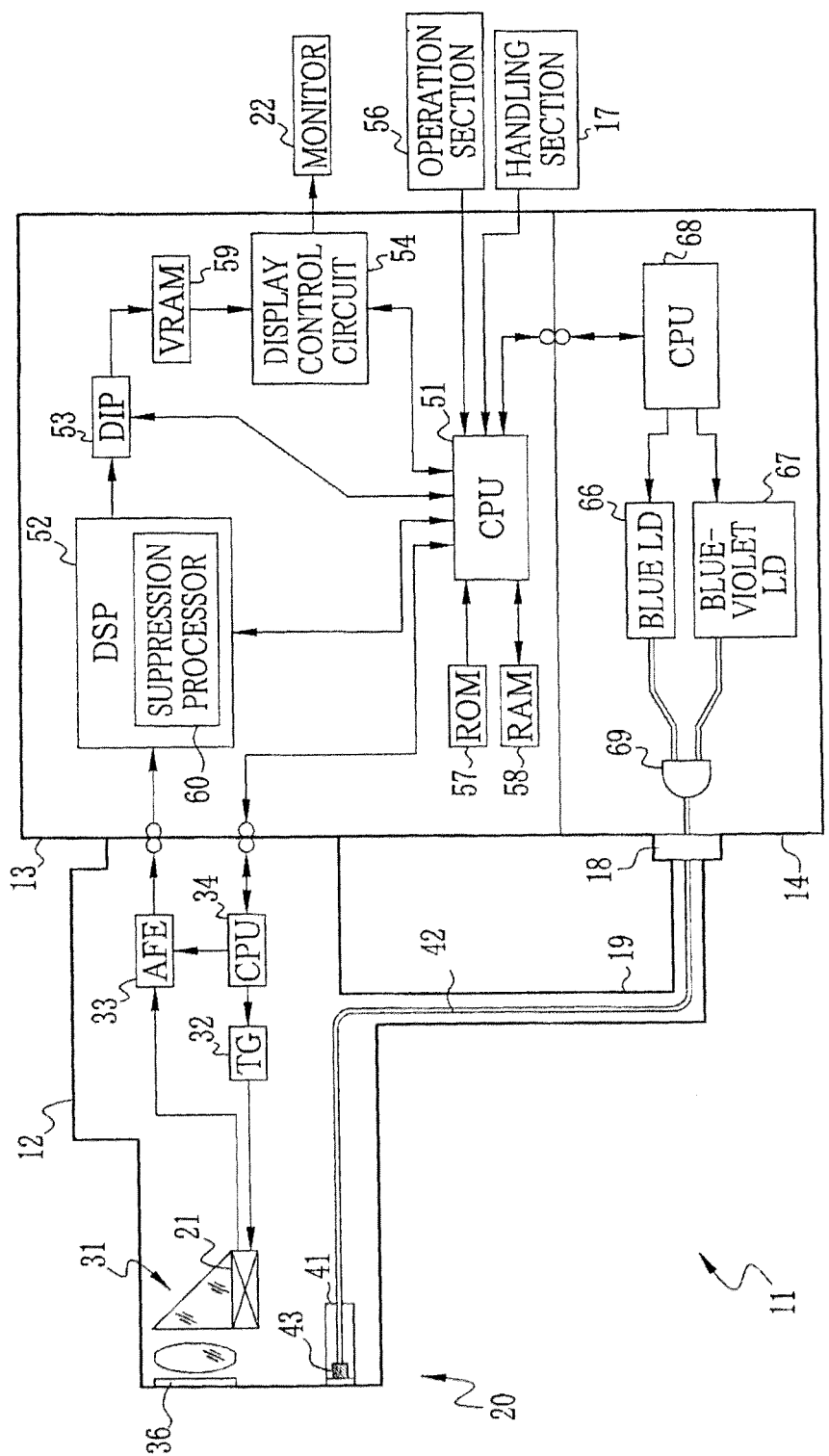
FIG. 2 is a block diagram showing an electric configuration of the electronic endoscope system.

As shown in FIG. 2, the distal portion 20 is provided with an objective optical system 31, a CCD21, and a projection unit 41, for example. A timing generator (hereinafter referred to as the TG) 32, an analog front-end circuit (hereinafter referred to as the AFE) 33, and a CPU 34 are provided to the handling section 17 or the connector 18, for example.

The objective optical system 31 is composed of a lens or a prism, for example. The objective optical system 31 forms an image of light reflected from the target portion and incident through a capture window 36 on the CCD 21.

The CCD 21 photoelectrically converts the image of the target portion on a pixel-by-pixel basis to accumulate signal charge corresponding to a quantity of the incident light. The CCD 21 outputs the signal charge, accumulated on the pixel-by-pixel basis, as the imaging signal. On each pixel of the CCD 21, a color filter composed of multiple color segments is formed. The color filter is a primary color filter (RGB filter) arranged in a Bayer pattern.

The TG 32 inputs a clock signal to the CCD 21. Based on the clock signal, the CCD 21 performs an accumulation operation and a read-out operation at predetermined timing. In the accumulation operation, the signal charge is accumulated. In the read-out operation, the signal charge accumulated is read out. The clock signal, outputted from the TG 32, is controlled by the CPU 34.

The AFE 33 is composed of a correlated double sampling (CDS) circuit, an automatic gain control (AGC) circuit, and an A/D conversion circuit (all not shown). The AFE 33 obtains an analog imaging signal from the CCD 21 while removing noise from the imaging signal. Then the AFE 33 performs gain correction to the imaging signal. Thereafter, the AFE 33 converts the imaging signal into a digital signal and inputs the digital signal to a DSP 52. The CDS circuit obtains the imaging signal while removing noise, caused by the CCD 21, through CDS processing. The AGC circuit amplifies the imaging signal inputted from the CDS circuit. The A/D conversion circuit converts the imaging signal, inputted from the AGC circuit, into a digital signal of predetermined bit, and then inputs the digital signal to the DSP 52. The operation of the AFE 33 is controlled by the CPU 34. For example, the CPU 34 controls a gain of the imaging signal in the AGC circuit based on a signal inputted from the CPU 51 of the processor apparatus 13.

The projection unit 41 applies or projects illumination light to the target portion. The projection unit 41 projects the normal light and the special light simultaneously as the illumination light to the target portion, which will be described later.

The projection unit 41 is provided with a phosphor 43. A light guide 42, composed of optical fibers, guides blue laser light and blue-violet laser light from the light source apparatus 14 to the phosphor 43. The phosphor 43 absorbs a part of the blue laser light and the blue-violet laser light to emit green to yellow fluorescence. The phosphor 43 is composed of YAG fluorescent substance or BAM(EaMgAl$_{10}$O$_{17}$) fluorescent substance, for example. A part of the blue laser light and the blue-violet laser light passes through the phosphor 43 without being absorbed. Accordingly, the projection unit 41 projects pseudo white light (normal light) in which the green to yellow fluorescence from the phosphor 43 and the blue light passed through the phosphor 43 are combined. The pseudo white light is projected as the illumination light to the target portion. Each of the blue light and the blue-violet light passed through the phosphor 43 functions as the special light.

Note that the blue laser light and the blue-violet laser light differ in fluorescence excitation efficiency of the phosphor 43. When a quantity of incident blue laser light is equal to that of incident blue-violet laser light, the blue laser light causes the phosphor 43 to generate a greater quantity of light than the blue-violet laser light does. The blue laser light is diffused while passing through the phosphor 43. This makes the normal light, projected from the projection unit 41, uniform across a field of view of the electronic endoscope 12.

The processor apparatus 13 has a CPU 51, the digital signal processor circuit (DSP) 52, a digital image processor (DIP) 53, a display control circuit 54, an operation section 56, and the like.

The CPU 51 is connected to each section through data bus, address bus, and control lines (all not shown) to control the entire processor apparatus 13. A ROM 57 stores various data such as programs (an OS, an application program, and the like) for controlling operation of the processor apparatus 13 and graphic data. The CPU 51 reads out a program or data from the ROM 57 and extends it on a RAM 58 that is a working memory, and executes the program sequentially. The CPU 51 retrieves information, for example, text information such as examination time and date, patient information, and operator information from the operation section 56 or a network such as LAN and stores the information in the RAM 58, on an examination by examination basis.

To generate image data, the DSP 52 performs various signal processes such as color separation, color interpolation, gain correction, white-balance adjustment, and gamma correction to the imaging signal inputted from the CCD 21 through the APE 33.

To perform the observation with the normal light, the DSP 52 generates normal light image data. In the normal light image data, a blue signal (hereinafter referred to as the B signal) outputted from a blue pixel of the CCD 21 is assigned to a blue picture element or pixel (hereinafter referred to as the B pixel). A green signal (hereinafter referred to as the G signal) outputted from a green pixel of the CCD 21 is assigned to a green picture element or pixel (hereinafter referred to as the G pixel). A red signal (hereinafter referred to as the R signal) outputted from a red pixel of the CCD 21 is assigned to a red picture element or pixel (hereinafter referred to as the R pixel). On the other hand, to perform the special light observation, the DSP 52 generates the special light image data. In the special light image data, the B signal is assigned to the B and G pixels. The G signal is assigned to the R pixel. In this case, the R signal is omitted except when a suppression processor 60 is functioning, which will be described later.

The DSP 52 is provided with the suppression processor 60 for generating subsurface vessel suppressed image data. The subsurface vessel suppressed image data is generated during the special light observation. In the subsurface vessel suppressed image data, the B signal is assigned to the B and G pixels. A signal value which is a sum of the R signal and the G signal is assigned to the R pixel. An addition rate of the R signal, being a pixel value of the R pixel, added to the G signal is determined depending on suppression degree representing an extent of suppression or reduction of the display of the subsurface blood vessel. To be more specific, the suppression degree is set previously as a parameter for image processing. The R signal to be added increases as the suppression degree increases. The R signal to be added decreases as the suppression degree decreases. The suppression processor 60 operates when the display of the subsurface blood vessel is to be suppressed or reduced.

The image data generated in the DSP 52 is inputted to the working memory of the DIP 53. The DSP 52 generates ALC data necessary for automatic level control (ALC) of a quantity of the illumination light. The ALC data includes, for example, an average brightness value of pixels in the image data generated. The DSP 52 inputs the ALC data in the CPU 51.

The DIP 53 performs various image processes such as electronic magnification and enhancement processing to the image data generated in the DSP 52. After being subjected to the image processes, the image data is temporarily stored as an observation image in a VRAM 59, and then inputted to the display control circuit 54.

To be more specific, the DIP 53 performs frequency enhancement processing according to a predetermined setting. The DIP 53 increases a pixel value of an image in a predetermined frequency band to improve the contrast thereof. The increase in the pixel value depends on properties of a target, for example, whether the target is the surface blood vessel or the subsurface blood vessel. The surface blood vessel is enhanced by improving the contrast of an image in a frequency band determined for the surface blood vessel.

Similarly, the subsurface blood vessel is enhanced by improving the contrast of an image in a frequency band determined for the subsurface blood vessel. However, when the subject distance (the distance between the distal portion 20 and a mucosa of the target portion) is long, the subsurface blood vessel shown in the image appear to be as narrow as the surface blood vessel. In this case, the frequency enhancement processing aiming at the surface blood vessel may enhance the subsurface blood vessel instead. On the other hand, when the subject distance is short, the surface blood vessel shown in the image appears to be as wide as the subsurface blood vessel. In this case, the frequency enhancement processing aiming at the subsurface blood vessel may enhance the surface blood vessel instead.

The display control circuit 54 obtains the observation image from the VRAM 59 and receives the graphic data and the like, stored in the ROM 57 and the RAM 58, from the CPU 51. The graphic data includes a display mask, text information, and a GUI. The display mask displays an effective pixel region with the target portion out of the observation image. The text information includes the examination time and date, the patient information, and the operator information. The display control circuit 54 superimposes the graphic data on the observation image. The display control circuit 54 converts the observation image into a video signal (a component signal, a composite signal, or the like) compliant with a display format of the monitor 22, and then outputs the video signal to the monitor 22. Thereby, the observation image is displayed on the monitor 22.

The operation section 56 is a known input device, for example, an operation panel, a mouse, and a keyboard provided to the processor apparatus 13. The CPU 51 controls each section of the electronic endoscope system 11 in response to an operation signal inputted through the operation section 56 or the handling section 17 of the electronic endoscope 12.

Additionally, the processor apparatus 13 is provided with a compression circuit, a media I/F, a network I/F, and the like (all not shown), connected to the CPU 51 through data bus or the like (not shown). The compression circuit compresses image data in a predetermined compression format (for example, JPEG format). The media I/F records the image, compressed in response to the operation of the release button, in a removable media. The network I/F performs data transmission between the processor apparatus 13 and the network such as LAN.

The light source apparatus 14 has two laser diodes, a blue LD 66 and a blue-violet LD 67, as the light source.

The blue LD 66 emits blue laser light at a center wavelength of 445 nm. The blue laser light is guided to the projection unit 41 through the connector 18 and the light guide 42 and then incident on the phosphor 43. The phosphor 43 absorbs a part of the incident blue laser light to emit fluorescence. The remaining light is diffused while passing through the phosphor 43. The fluorescence and the blue light passed through the phosphor 43 are applied as pseudo white light to the target portion. A light quantity of the blue light is larger than that caused by the phosphor 43. The blue light also functions as the special light, which is well-absorbed by blood in the surface blood vessel.

The blue-violet LD 67 emits blue-violet laser light at a center wavelength of 405 nm. A combiner 69 combines the blue-violet laser light with the blue laser light. Similar to the blue laser light, the blue-violet laser light is guided to the projection unit 41 through the connector 18 and the light guide 42. The blue-violet laser light, upon incidence on the phosphor 43, generates pseudo white light to be applied to the target portion. However, a quantity of the white light generated by applying the blue-violet laser light is generally smaller than that by the blue laser light. The light not absorbed by the phosphor 43 is diffused while passing through the phosphor 43. The blue-violet light also functions as the special light.

Emission timing and a quantity of light from each of the blue LD 66 and the blue-violet LD 67 is controlled by a CPU 68. For example, the CPU 68 may turn on only the blue LD 66 to perform the normal light observation. The CPU 68 may turn on both the blue LD 66 and the blue-violet LD 67 to perform the special light observation. The CPU 68 automatically controls the quantities of light from the blue LD 66 and the blue-violet LD 67 realtime based on ALC data inputted from the CPU 51 of the processor apparatus 13.

Here, the above-configured electronic endoscope system 11 turns on both the blue LD 66 and the blue-violet LD 67 regardless of whether the normal light observation or the special light observation is performed. Thereby, the white light and the special light (the blue light and blue-violet light) are projected simultaneously as the illumination light from the projection unit 41 to the target portion. The quantities of light emitted from the respective blue LD 66 and blue-violet LD 67, and the light quantity ratio between the LDs 66 and 67 depends on whether the normal light observation or the special light observation is performed, or whether the surface blood vessel or the subsurface blood vessel is enhanced when the special light observation is performed, for example.

During the normal light observation, the electronic endoscope system 11 generates the normal light image data by using the B, G, and R signals outputted from the CCD 21 for the B, G, and R pixels, respectively. The DIP 53 performs various image processes to the normal light image data. Then, the display control circuit 54 superimposes the graphic data and the like onto the normal light image data. Thereafter, a normal light image is displayed on the monitor 22.

Figure 3:
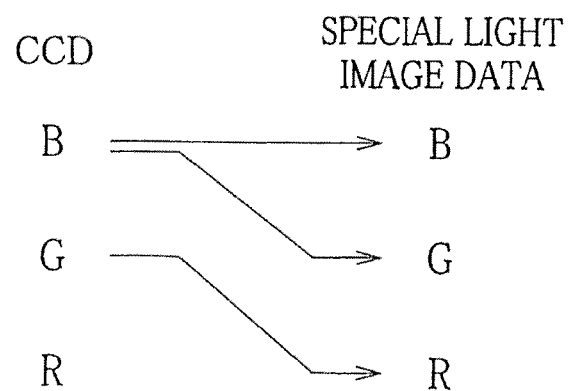
FIG. 3 is an explanatory view showing generation of special light image data from an imaging signal.

On the other hand, during the special light observation, as shown in FIG. 3, the electronic endoscope system 11 generates the special light image data by using the B signal outputted from the CCD 21 for the B and G pixels, and the G signal outputted from the CCD 21 for the R pixel. Thereby, the blood vessels are more enhanced in the special light image data than in the normal light image data. This is because optical absorption of hemoglobin in blood has a peak in wavelength ranges of the blue light and the green light, which improves the contrast of the blood vessel(s) in the B signal corresponding to the blue light and that in the G signal corresponding to the green light. The DIP 53 performs various image processes to the special light image data. Then, the display control circuit 54 superimposes the graphic data and the like onto the special light image data. Thereafter, a special light image is displayed on the monitor 22.

Figure 4:
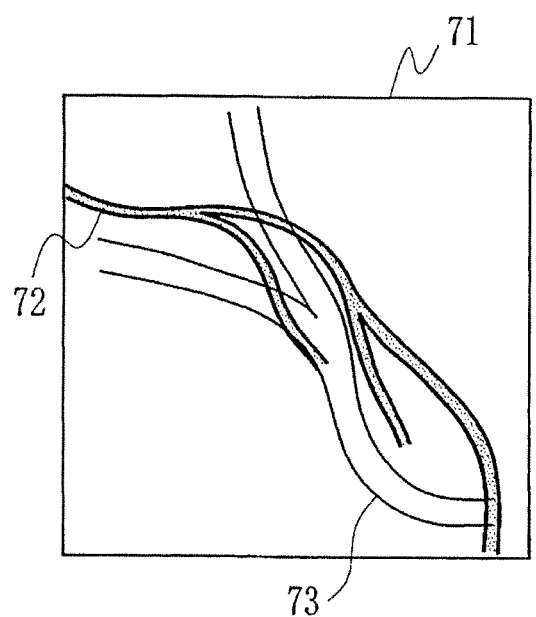
FIG. 4 is a schematic diagram showing a surface blood vessel and a subsurface blood vessel shown in the special light image data.

As shown in FIG. 4, a surface blood vessel 72 is enhanced in special light image data 71 by way of example. The special light image data 71 also includes a subsurface blood vessel 73. The surface blood vessel 72 is superposed on the subsurface blood vessel 73, which may hinder the observation of the surface blood vessel 72 even if the surface blood vessel 72 has been enhanced. When the special light image data 71 is subjected to the frequency enhancement processing in the DIP 53, the subsurface blood vessel 73 may be enhanced instead of the surface blood vessel 72 depending on the subject distance. This further hinders the observation of the surface blood vessel 72.

In such cases, the electronic endoscope system 11 suppresses or reduces the display of the subsurface blood vessel 73. To be more specific, the setting for suppressing the display of the subsurface blood vessel 73 is turned on by operating the operation section 56. At the same time, a degree of suppression (hereinafter referred to as the suppression degree) is set as a parameter for the image processing. The suppression degree represents the extent of suppressing or reducing the display of the subsurface blood vessel 73. The suppression degree is set as a numerical value from 1 to 100, for example. The display of the subsurface blood vessel 73 is more suppressed or reduced as the suppression degree increases. The image of the subsurface blood vessel 73 remains similar to the image captured as the suppression degree decreases.

Figure 5:
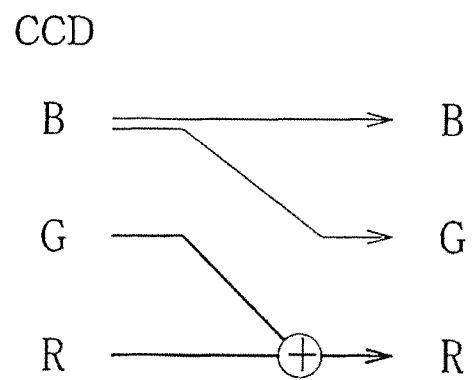
FIG. 5 is an explanatory view showing how to reduce contrast of the subsurface blood vessel.

When the setting for suppressing the display of the subsurface blood vessel 73 is turned on, the suppression processor 60 operates when the DSP 52 generates the special light image data 71 from the imaging signal inputted from the CCD 21. As shown in FIG. 5, the suppression processor 60 uses the B signal outputted from the CCD 21 for the B and G pixels. The signal value which is the sum of the R signal and the G signal is used for the pixel value of the R pixel. Thus, the DSP 52 generates the subsurface vessel suppressed image data.

Because the subsurface blood vessel 73 is located under a mucosa and deeper than the surface blood vessel 72, the subsurface blood vessel 73 mainly absorbs the green light with large penetration depth. Accordingly, the subsurface blood vessel 73 shows contrast in the G signal. On the other hand, because the surface blood vessel 72 is shallower than the subsurface blood vessel 73, the surface blood vessel 72 is likely to absorb the blue light with small penetration depth. Accordingly, the surface blood vessel 72 shows contrast mainly in the B signal. Because hemoglobin absorbs a small quantity of light in a wavelength range of red light, both the contrast of the surface blood vessel 72 and the contrast of the subsurface blood vessel 73 are small in the R signal.

Figure 6:
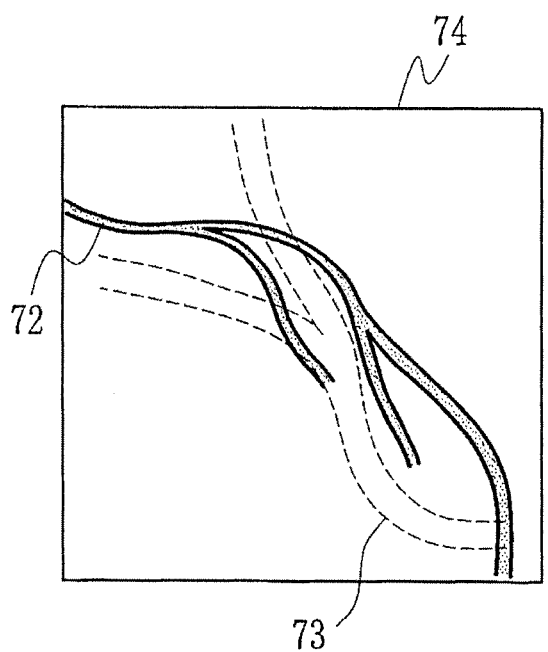
FIG. 6 is a schematic view of the special light image data in which display of the subsurface blood vessel is suppressed.

In the subsurface vessel suppressed image data, R signal showing the subsurface blood vessel 73 in low contrast is added to the G signal showing the subsurface blood vessel 73 in high contrast. Thereby, a signal value in which a component of the G signal is relatively reduced is used as the pixel value of the R pixel. Thereby, as shown in FIG. 6, in subsurface vessel suppressed image data 74, the contrast of the image of the subsurface blood vessel 73 is reduced. On the other hand, the surface blood vessel 72 gets reflected mainly in the B signal. The contrast of the image of the surface blood vessel 72 is shown in the B and G pixels. Accordingly, similar to the special light image data, the surface blood vessel 72 is enhanced in the subsurface vessel suppressed image data. Thus, the visibility of the surface blood vessel 72 improves in the subsurface vessel suppressed image data 74.

The suppression processor 60 adjusts the addition rate of the R signal in accordance with the set suppression degree. For example, a value of the R signal added to the G signal increases as the suppression degree increases. The contrast of the image of the subsurface blood vessel 73 decreases as the value of the R signal added to the G signal increases. Thereby, the subsurface blood vessel 73 is displayed with the visibility corresponding to the set suppression degree.

Similar to the special light image data 71, the DIP 53 performs various image processes to the subsurface vessel suppressed image data 74. Then, the display control circuit 54 superimposes the graphic data and the like on the subsurface vessel suppressed image data 74. Thereafter, a subsurface vessel suppressed image is displayed on the monitor 22. As described above, when the DIP 53 performs the frequency enhancement processing to the image data generated in the DSP 52, non-target tissue (here, the subsurface blood vessel 73) may be enhanced instead of a target blood vessel depending on the subject distance. Even so, the frequency enhancement processing has little effect on the subsurface vessel suppressed image data 74 because the contrast of the subsurface blood vessel 73 is reduced in accordance with the suppression degree.

In the first embodiment, the R signal is added to the G signal, which changes a color tone of the subsurface vessel suppressed image data 74 relative to that of the special light image data 71.

Figure 7A:
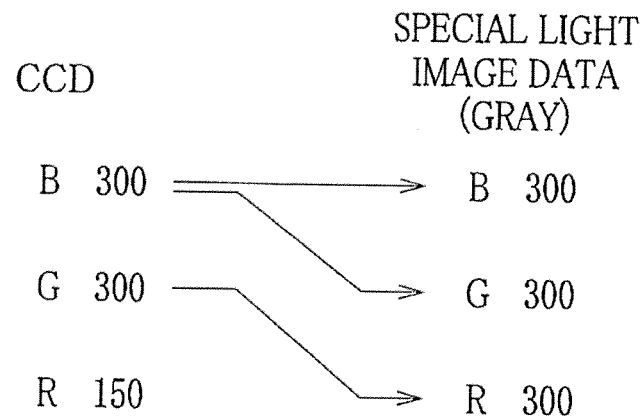
FIG. 7A is an explanatory view showing color tone of the special light image data.

For example, as shown in FIG. 7A, signal values of color signals of the CCD 21 satisfy the following when an image is captured under illumination light of a predetermined condition.

B signal:G signal:R signal=300:300:150

The DSP 52 generates the special light image data 71 from the image signals of respective colors and adjusts the color tone so as not to hinder the observation. For the sake of easy explanation, the signal value of the B signal is used for each of the B, and G pixel values of the special light image data 71. The signal value of the G signal is used for R pixel value of the special light image data 71. Thereby, the special light image data 71 is gray image data in which each of the B, G, and R pixel values is "300" and equal to one another.

Figure 7B:
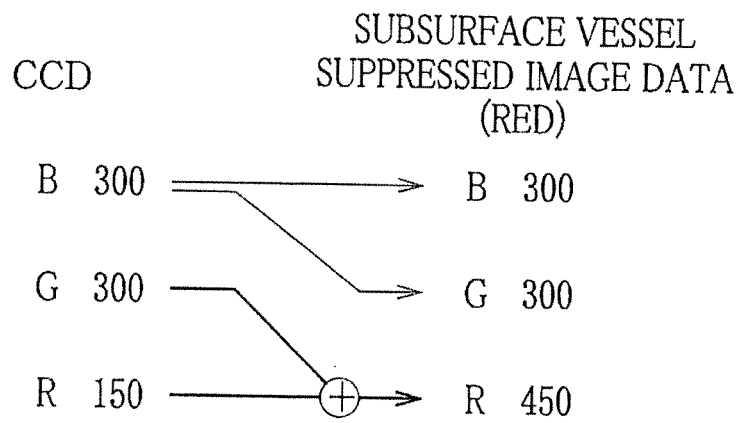
FIG. 7B is an explanatory view showing color tone of subsurface vessel suppressed image data.

On the other hand, as shown in FIG. 7B, the subsurface vessel suppressed image data 74 is generated under the illumination of the condition similar to the above. Each of the pixel values of the B and G signals is "300", which is equal to those of the special light image data 71. The pixel value of the R pixel is "450" that is the sum of the R signal and the G signal. For this reason, the color of the entire subsurface vessel suppressed image data 74 becomes reddish when the subsurface vessel suppressed image data 74 is generated in a similar manner to the special light image data 71.

Accordingly, to generate the subsurface vessel suppressed image data 74, it is preferable to correct its color tone to be similar to that of the special light image data 71. The color tone is corrected in the following three ways by way of example.

Figure 8:
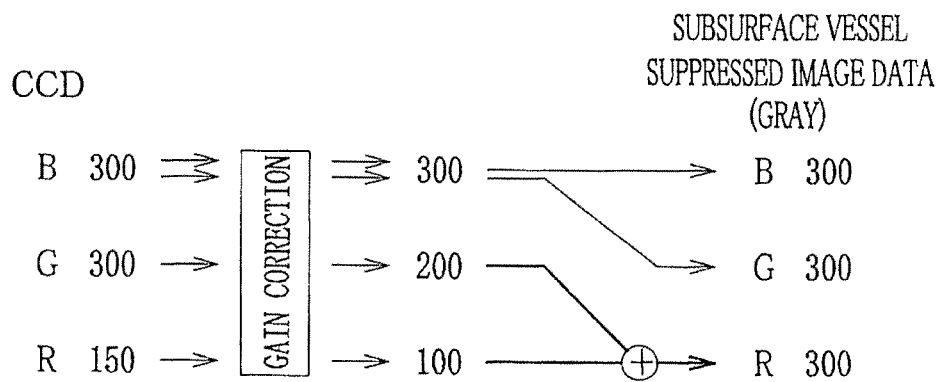
FIG. 8 is an explanatory view showing color tone correction of the subsurface vessel suppressed image data.

As shown in FIG. 8, before the generation of the subsurface vessel suppressed image data 74, gain correction (taking into account the suppression degree) is performed to the B, G, and R imaging signals to generate the subsurface vessel suppressed image data 74 in a predetermined color tone (gray). Thereby, the color tone of the subsurface vessel suppressed image data 74 is corrected.

In generating the subsurface vessel suppressed image data 74, when the set suppression degree requires addition of the G signal and the R signal at a ratio of 1:1, the gain correction is performed to make the signal value of the B signal "200" and the signal value of the R signal "100". Thereby, the signal values satisfy the following.

B signal:G signal:R signal=300:200:100

Based on these signal values, the subsurface vessel suppressed image data 74 is generated. The pixel values of respective pixels in the subsurface vessel suppressed image data 74 satisfy the following.

B pixel:G pixel:R pixel=300:300:300

Thereby, similar to the special light image data 71, the subsurface vessel suppressed image data 74, being the gray image data, is generated.

Note that the gain correction may be performed to the imaging signals, outputted from the CCD 21, in the AFE 33. Alternatively, the gain correction may be performed to the imaging signals, outputted from the CCD 21, in the DSP 52.

Figure 9:
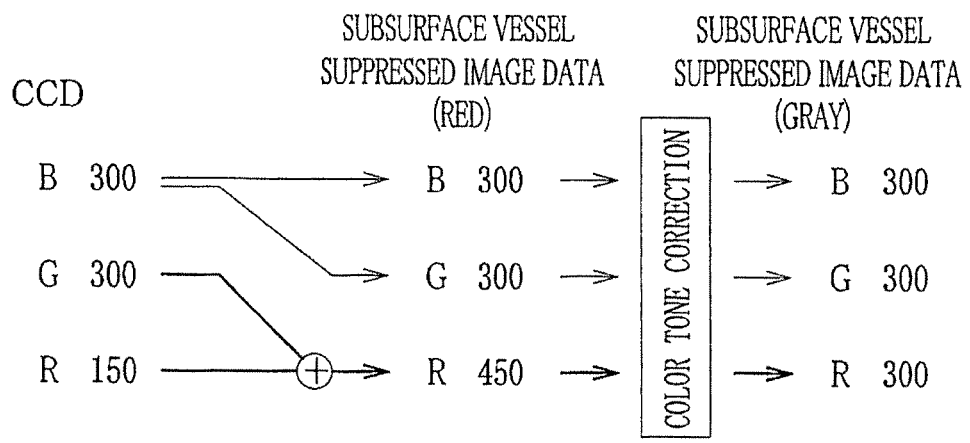
FIG. 9 is an explanatory view showing color tone correction of the subsurface vessel suppressed image data.

As shown in FIG. 9, after the subsurface vessel suppressed image data 74 is generated, the color tone of subsurface vessel suppressed image data 74 may be corrected to be similar to that of the special light image data 71 through color tone correction. For example, the imaging signals of respective colors inputted from the CCD 21 are used without correction to generate the subsurface vessel suppressed image data 74 in accordance with the suppression degree. This subsurface vessel suppressed image data 74 has reddish color as described above. So, the color tone correction is performed to correct the pixel value of the R pixel, of the reddish subsurface vessel suppressed image data 74, to "300". Thus, the gray subsurface vessel suppressed image data 74 is generated.

Figure 10:
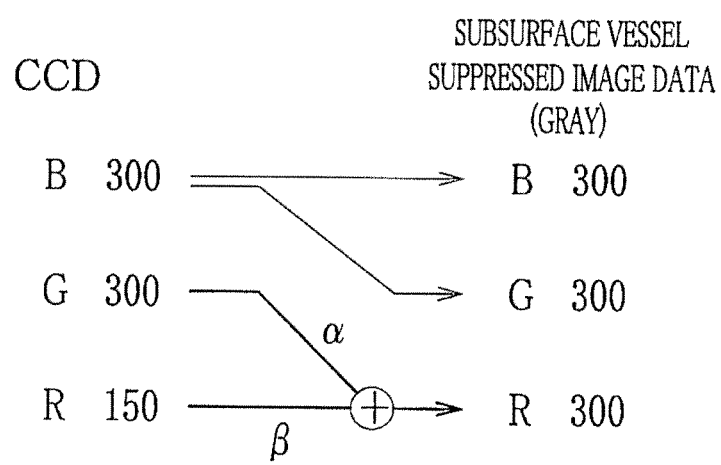
FIG. 10 is an explanatory view showing color tone correction of the subsurface vessel suppressed image data.

As shown in FIG. 10, before the R signal is added to the G signal, the G signal is multiplied by a coefficient $\alpha$, and the R signal is multiplied by a coefficient $\beta$, so as to set the pixel value of the R pixel to a predetermined value ("300", for example). Thereby, the gray subsurface vessel suppressed image data 74 is generated. Each of the coefficients $\alpha$ and $\beta$ is previously determined based on the quantity of illumination light, the suppression degree, or the like. For example, when the illumination light causes a ratio between the G signal and the R signal to be "2:1 (=300:150)", and the G signal and the R signal are added without correction, the pixel value of the R pixel is set to "300" and each of the coefficients $\alpha$ and $\beta$ is set to "⅔" to obtain the gray subsurface vessel suppressed image data 74.

The color tone correction may be performed easily by previously providing different lookup tables (LUTs) for the color tone correction, each corresponding to the suppression degree or the like. The look up table to be used is selected based on the suppression degree. To perform the color tone correction using calculation, different matrices (MTXs) for calculation may be provided previously. The color tone correction of the subsurface vessel suppressed image data 74 using the gain correction may be performed in a similar manner. Different LUTs for determining a gain corresponding to the suppression degree and different MTXs for calculating the gain corresponding to the suppression degree from a predetermined gain may be provided previously. The coefficients $\alpha$ and $\beta$ may be provided previously in a similar manner.

In the first embodiment, the suppression processor 60 is used to suppress or reduce the display of the subsurface blood vessel 73, for example. Alternatively, the suppression processor 60 may be used to suppress or reduce the display of the surface blood vessel 72. In the first embodiment, to suppress or reduce the display of the subsurface blood vessel 73, the contrast of the subsurface blood vessel 73 is reduced. To reduce the contrast, the R signal in which the subsurface blood vessel 73 shows low contrast is added to the G signal in which the subsurface blood vessel 73 shows high contrast. On the other hand, to suppress or reduce the display of the surface blood vessel 72, the R or G signal in which the surface blood vessel 72 shows low contrast is added to the B signal in which the surface blood vessel 72 shows high contrast. Note that the signal processing using the suppression processor 60 is suitable for suppressing the display of the subsurface blood vessel 73. To suppress or reduce the display of the surface blood vessel 72, it is preferable to apply the invention of a second embodiment, which will be described later.

In the first embodiment, the display of the subsurface blood vessel 73 is suppressed or reduced by way of example. In the second embodiment, on the other hand, the display of the surface blood vessel 72 is suppressed or reduced to observe the subsurface blood vessel 73. Parts similar to those in the electronic endoscope system 11 of the first embodiment are designated with similar reference numerals, and descriptions thereof are omitted.

Second Embodiment

Figure 11:
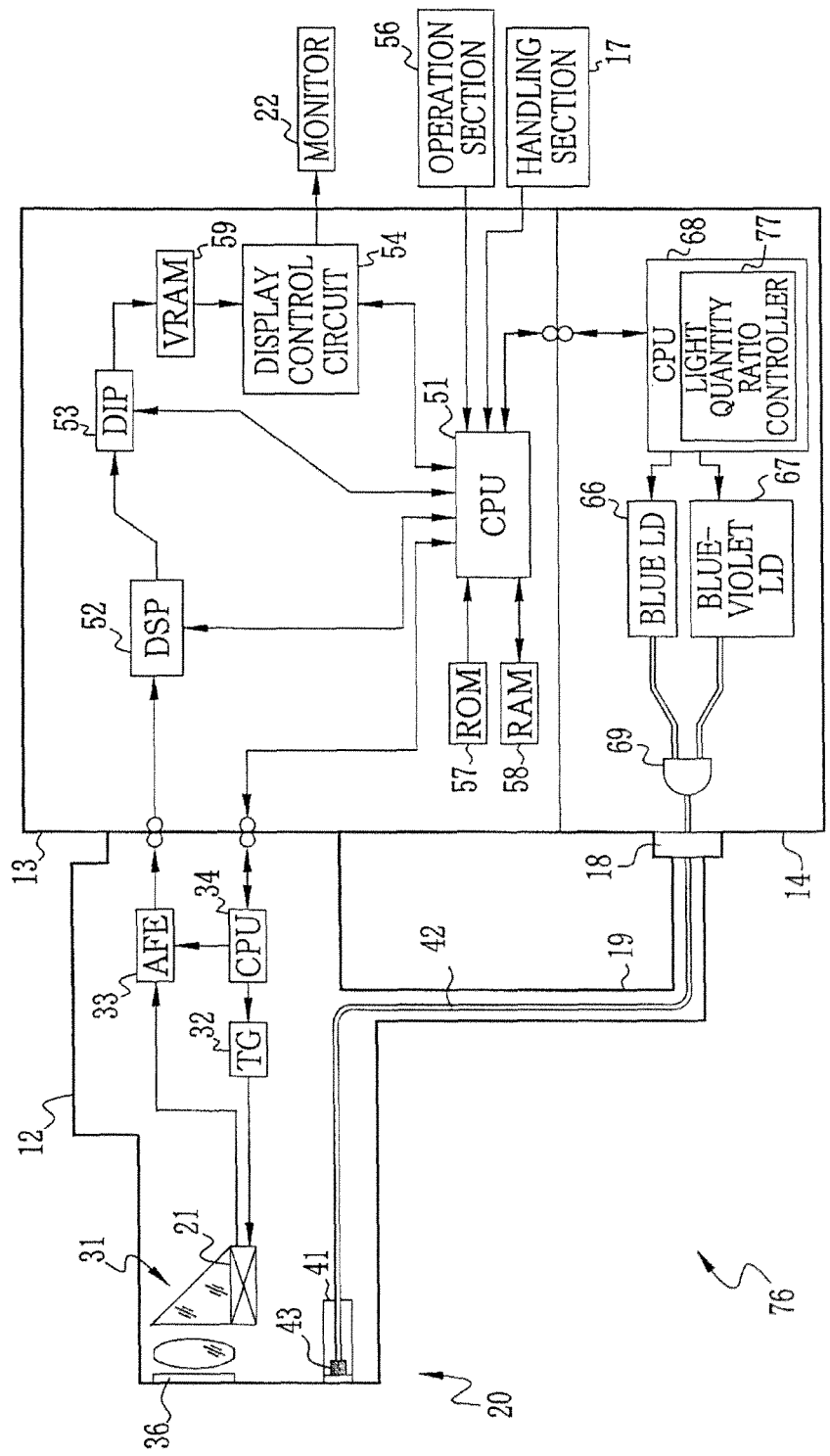
FIG. 11 is a block diagram showing an electric configuration of an electronic endoscope system of a second embodiment.

As shown in FIG. 11, an electronic endoscope system 76 suppresses or reduces the display of the surface blood vessel 72 according to a setting. The CPU 68 of the light source apparatus 14 is provided with a light quantity ratio controller 77.

The light quantity ratio controller 77 controls a light quantity ratio between the quantity of the light from the blue LD 66 and the quantity of the light from the blue-violet LD 67. The light quantity ratio is controlled based on the light quantity of the whole illumination light determined by the ALC and the set suppression degree. Thereby, the spectrum of the illumination light is changed to reduce the contrast of the surface blood vessel 72. The suppression degree is a parameter representing the extent of suppressing or reducing the display of the surface blood vessel 72. For example, the suppression degree is set previously by inputting a numerical value. The light quantity ratio controller 77 reduces the contrast of the surface blood vessel 72. The light quantity ratio controller 77 operates when the suppression of the display of the surface blood vessel 72 is set.

To be more specific, the light quantity ratio controller 77 increases the quantity of the light from the blue LID 66 relative to that from the blue-violet LID 67. The relative increase rate of the quantity of the light from the blue LID 66 is determined in accordance with the set suppression degree. The light quantity ratio controller 77 controls the light quantity ratio between the blue LID 66 and the blue-violet LID 67 to regulate the light quantity of the normal light projected from the projection unit 41 at a value determined by the ALC. According to the ALC, the light quantity ratio between the blue LID 66 and the blue-violet LID 67 is adjusted by increasing and/or decreasing the quantity of the light from the blue-violet LD 67.

The operations of the electronic endoscope system 76 during the normal light observation and the special light observation with no display suppression of the surface blood vessel 72 are similar to those of the electronic endoscope system 11 in the first embodiment. To suppress or reduce the display of the surface blood vessel 72 during the special light observation, the electronic endoscope system 76 operates as follows.

To suppress or reduce the display of the surface blood vessel 72, first, the operation section 56 and the like are operated to turn on the setting for suppressing the display of the surface blood vessel 72 and to set the suppression degree. The suppression degree is set as a numerical value from 1 to 100, for example. The display of the surface blood vessel 72 is more suppressed or reduced as the suppression degree increases. The display of the surface blood vessel 72 remains similar to the image captured as the suppression degree decreases.

Next, the light quantity ratio controller 77 operates when the setting for suppressing the display of the surface blood vessel 72 is turned on and the suppression degree is set. Thereby, the light quantity ratio controller 77 increases the quantity of the light from the blue LD 66 relative to that from the blue-violet LD 67 while regulating the light quantity of the normal light in the illumination light at a predetermined value based on the ALC.

Figure 12:
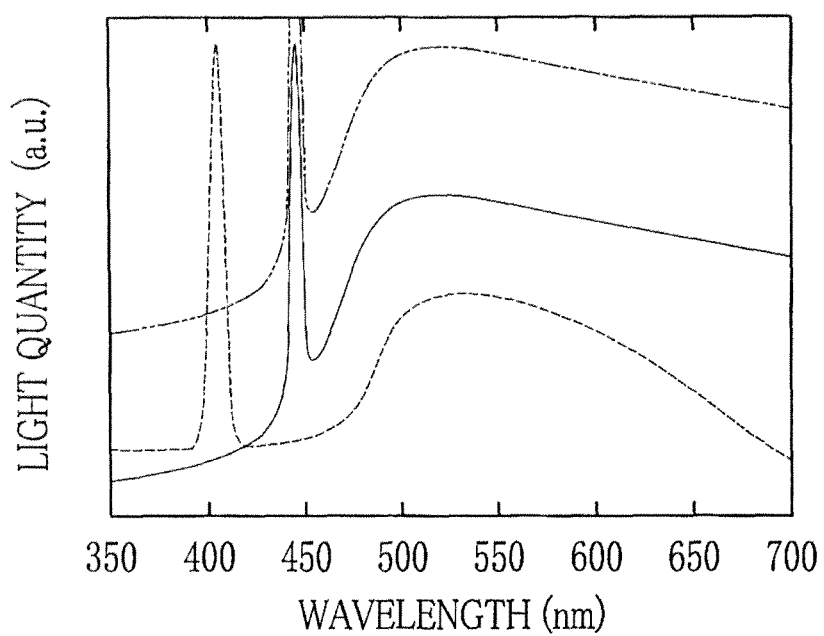
FIG. 12 is a graph showing a relationship between a wavelength of light incident on a phosphor and a light quantity of fluorescence generated.

As shown by a solid line and a broken line in FIG. 12, light quantities of the fluorescence from the phosphor 43 generated by the excitation differ between the blue-violet laser light (405 nm) from the blue-violet LD 67 and the blue laser light (445 nm) from the blue LD 66. To be more specific, the blue laser light has higher fluorescence excitation efficiency than the blue-violet laser light.

As shown by a two-dot chain line in FIG. 12, when the quantity of the light from the blue LD 66 increases, a component of the normal light increases in the light quantity of the illumination light. Thereby, a proportion of the light quantities of the blue-violet light (405 nm) and the blue light (445 nm), being the special light, is reduced relative to the light quantity of the whole illumination light.

The surface blood vessel 72 absorbs the special light. Thereby, the contrast of the surface blood vessel 72 is shown in the B signal. The contrast of the image of the surface blood vessel 72 decreases when the proportion of the light quantity of the special light decreases relative to the light quantity of the whole illumination light. As a result, the visibility of the surface blood vessel 72 declines. On the other hand, the contrast of the subsurface blood vessel 73 is shown mainly in the G signal. Accordingly, there is substantially no change in the contrast of the subsurface blood vessel 73 even if the light quantity ratio between the blue LD 66 and the blue-violet LD 67 is changed. Thus, the observability of the subsurface blood vessel 73 does not change substantially regardless of whether the light quantity ratio controller 77 is functioning or not.

Figure 13B:
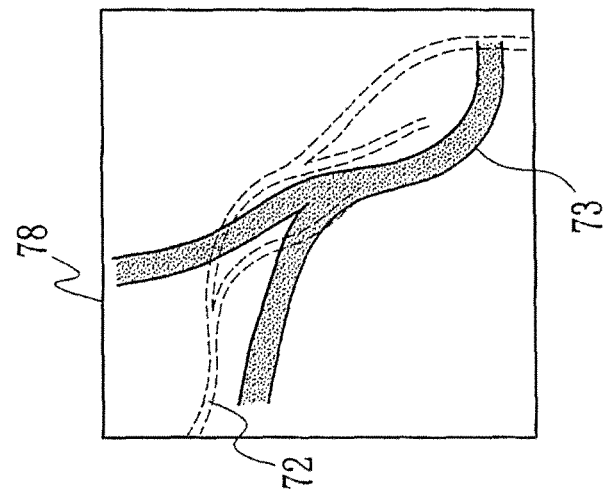
FIG. 13B is an explanatory view showing display suppression of the surface blood vessel of FIG. 13A by way of example.
Figure 13A:
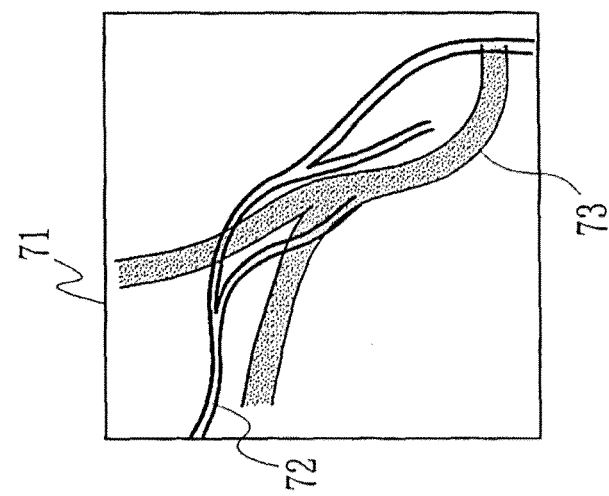
FIG. 13A is an explanatory view showing an example in which the surface blood vessel is superposed on the subsurface blood vessel.

As shown in FIG. 13A, when the setting for suppressing the display of the surface blood vessel 72 is turned off, the surface blood vessel 72 is superposed on the subsurface blood vessel 73 in the special light image data 71. In this case, the surface blood vessel 72 may hinder the observation of the subsurface blood vessel 73. On the other hand, as shown in FIG. 13B, when the setting for suppressing the display of the surface blood vessel 72 is turned on, special light image data (hereinafter referred to as the surface vessel suppressed image data) 78 is generated. In the surface vessel suppressed image data 78, the display of the surface blood vessel 72 is suppressed or reduced. As a result, the visibility of the subsurface blood vessel 73 improves relative to that of the surface blood vessel 72.

According to the image processing setting, the DIP 53 may perform the frequency enhancement processing to the surface vessel suppressed image data 78. In this case, depending on the subject distance, in the special light image data 71 with no suppression to the display of the surface blood vessel 72, the surface blood vessel 72 may be enhanced instead of the subsurface blood vessel 73 being the target blood vessel. This hinders the observation of the subsurface blood vessel 73. On the other hand, in the surface vessel suppressed image data 78, the contrast of the surface blood vessel 72 is reduced in accordance with the suppression degree. So, even if the surface blood vessel 72 is enhanced by the frequency enhancement processing, it affects the observation of the subsurface blood vessel 73 less in the surface vessel suppressed image data 78 than in the special light image data 71.

Note that in the second embodiment, the quantity of the light from the blue LD 66 and the quantity of the light from the blue-violet LD 67 are changed. This changes the color tone of the surface vessel suppressed image data 78 relative to that of the special light image data 71.

Figure 14A:
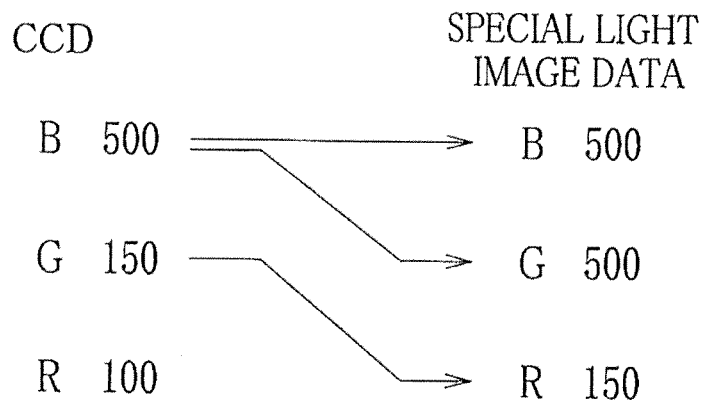
FIG. 14A is an explanatory view showing color tone of the special light image data.

For example, as shown in FIG. 14A, when an image is captured under illumination light of a predetermined condition, the signal values of respective color signals from the CCD 21 are as follows.

B signal:G signal:R signal=500:150:100

The DSP 52 generates the special light image data from the image signals with the corrected color tone so as not to hinder the observation. Here, for the sake of easy explanation, the signal value of the B signal is used for each of the B and G pixel values in the special light image data 71. The signal value of the G signal is used for the R pixel value in the special light image data 71. In this case, a ratio among pixel values in respective pixels in the special light image data 71 is as follows.

B pixel:G pixel:R pixel=500:500:150

Thereby, the special light image data 71 is displayed in cyan.

Figure 14B:
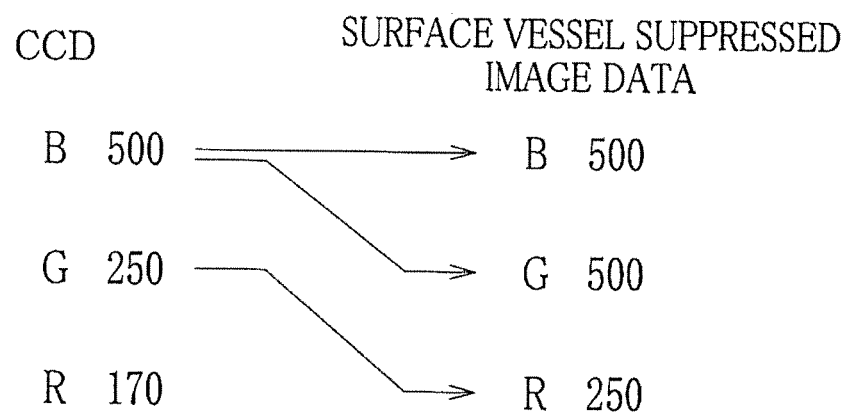
FIG. 14B is an explanatory view showing color tone of the surface vessel suppressed image data.

On the other hand, as shown in FIG. 14B, when the light quantity ratio between the blue LD 66 and the blue-violet LD 67 is changed while the light quantity of the whole illumination light is kept constant, signal values of respective color signals from the CCD 21 change. Here, when the light quantity ratio controller 77 adjusts the light quantity ratio between the blue LD 66 and the blue-violet LD 67, the signal values are changed as follows, for example.

B signal:G signal:R signal=500:250:170

In this case, a ratio among pixel values in respective pixels in the surface vessel suppressed image data 78 is as follows.

B pixel:G pixel:R pixel=500:500:250

The surface vessel suppressed image data 78 is displayed in cyan color lighter or paler than that in the special light image data 71.

As described above, in generating the surface vessel suppressed image data 78, when the light quantity ratio between the blue LD 66 and the blue-violet LD 67 is adjusted or changed by the light quantity ratio controller 77, it is preferable to correct the color tone of the surface vessel suppressed image data 78 similar to that of the special light image data 71. The color tone correction may be performed in the following three ways, for example.

Figure 15:
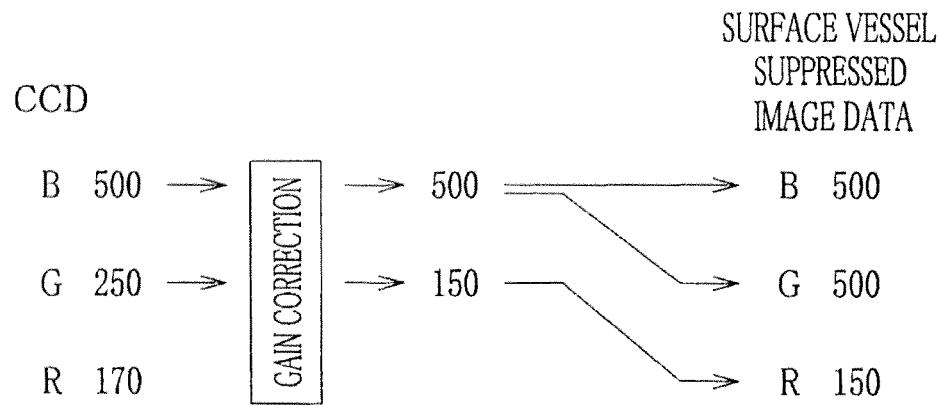
FIG. 15 is an explanatory view showing an example of color tone correction of the surface vessel suppressed image data.

As shown in FIG. 15, first, before the generation of the surface vessel suppressed image data 78, the gain correction (taking into account the suppression degree) is performed to the B, G, and R imaging signals such that the surface vessel suppressed image data 78 is generated in a predetermined color tone (cyan similar to the special light image data 71). Thereby, the color tone of the surface vessel suppressed image data 78 is corrected. The gain correction may be performed to the imaging signals, outputted from the CCD 21, in the AFE 33. The gain correction may be performed to the imaging signals in the DSP 52.

Figure 16:
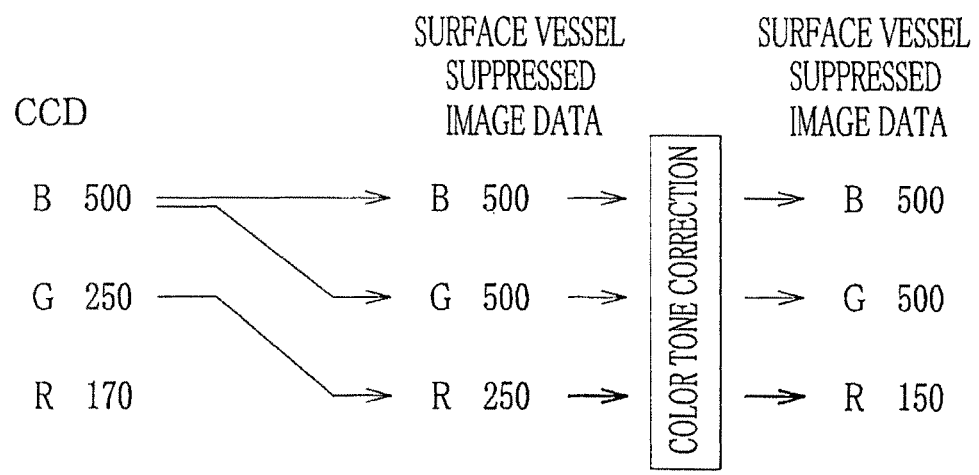
FIG. 16 is an explanatory view showing another example of color tone correction of the surface vessel suppressed image data.

Alternatively, as shown in FIG. 16, the color tone of the surface vessel suppressed image data 78 may be corrected to be similar to that of the special light image data 71 after the surface vessel suppressed image data 78 is generated.

Figure 17:
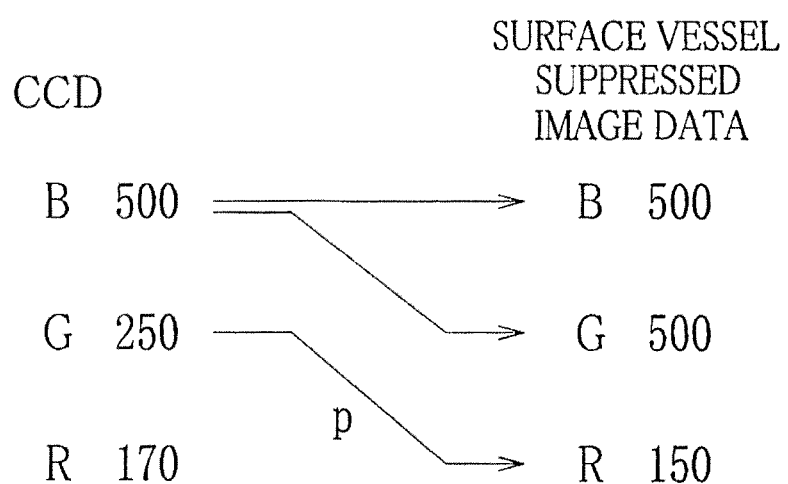
FIG. 17 is an explanatory view showing further another example of color tone correction of the surface vessel suppressed image data.

Alternatively, as shown in FIG. 17, a coefficient p may be determined previously in accordance with the light quantity ratio between the blue LD 66 and the blue-violet LD 67. A value obtained by multiplying the G signal by the coefficient p is used as the pixel value for the R pixel. This also corrects the color tone of the surface vessel suppressed image data 78.

The color tone correction may be performed easily by previously providing different look up tables (LUTs) for the color tone correction each corresponding to the suppression degree or the like. The look up table to be used is selected based on the suppression degree. To perform the color tone correction using calculation, different matrices (MTXs) for calculation may be provided previously. The color tone correction of the surface vessel suppressed image data 78 using the gain correction may be performed in a similar manner. Different LUTs for determining a gain corresponding to the suppression degree and different MTXs for calculating the gain corresponding to the suppression degree from a predetermined gain may be provided previously. The color correction is performed in the similar manner when the coefficient p is used.

In the second embodiment, the display of the surface blood vessel 72 is suppressed or reduced using the characteristic of the phosphor 43. Namely, the quantity of the light from the blue LD 66 is increased relative to the quantity of the light from the blue-violet LD 67. Alternatively or in addition, the display of the surface blood vessel 72 may be suppressed in a different manner, for example, by controlling a component of the illumination light.

Figure 18:
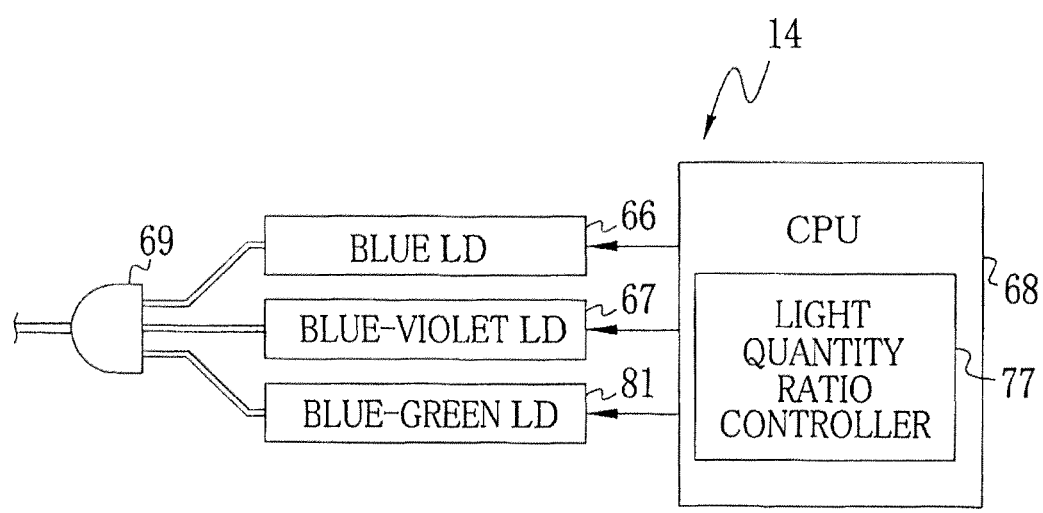
FIG. 18 is a block diagram showing a light source apparatus of another example.

For example, as shown in FIG. 18, the light source apparatus 14 is provided with a blue-green LD 81, being a third laser diode, used for suppressing or reducing the display of the surface blood vessel 72. The blue-green LD 81 is a light source which emits blue-green laser light at a wavelength of 473 nm. The blue-green laser light is combined with the light from the blue LD 66 and the blue-violet LD 67 through the combiner 69. The combined light, being the illumination light, is projected from the projection unit 41 to the target portion. The blue-green laser light is diffused while passing through the phosphor 43, and then applied uniformly as the blue-green illumination light to the field of view. The blue-green LD 81 is turned on to suppress or reduce the display of the surface blood vessel 72. In other words, the blue-green LD 81 is kept turned off in the normal light observation and the like.

Figure 19:
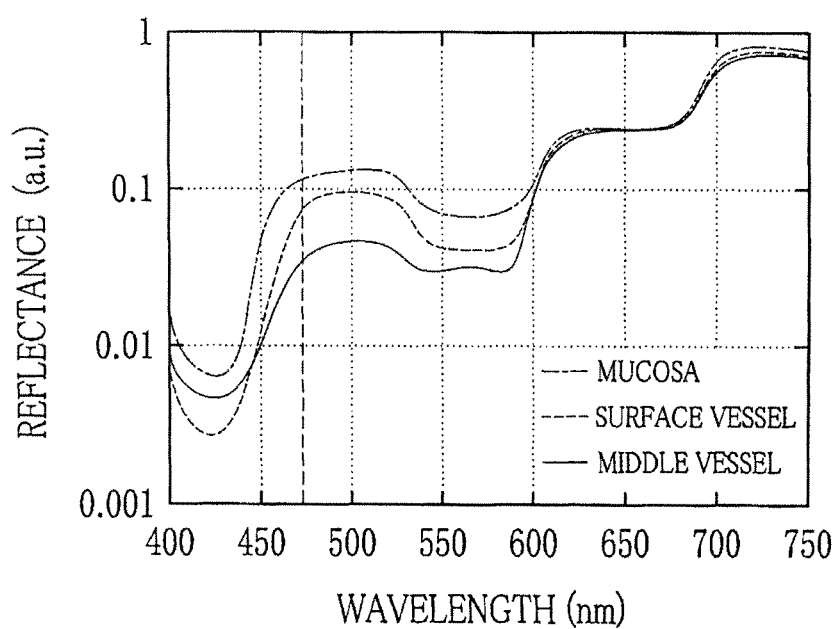
FIG. 19 is a graph showing reflectances of a mucosa, a surface blood vessel, and a subsurface blood vessel.

As shown in FIG. 19, reflectance of the surface blood vessel 72 is relatively higher than that of the subsurface blood vessel 73 at the wavelength (473 nm) of the blue-green light. A difference between the reflectance of the surface blood vessel 72 and that of the subsurface blood vessel 73 is large at the wavelength (473 nm) of the blue-green light when compared with light in a different wavelength range. Accordingly, by adding the blue-green light to the illumination light, the contrast of the surface blood vessel 72 is reduced relative to that of the subsurface blood vessel 73. Thus, the display of the surface blood vessel 72 is suppressed or reduced. With the use of the blue-green light, on the other hand, the image of the subsurface blood vessel 73 is obtained with higher contrast compared with the case without the blue-green light.

Figure 20:
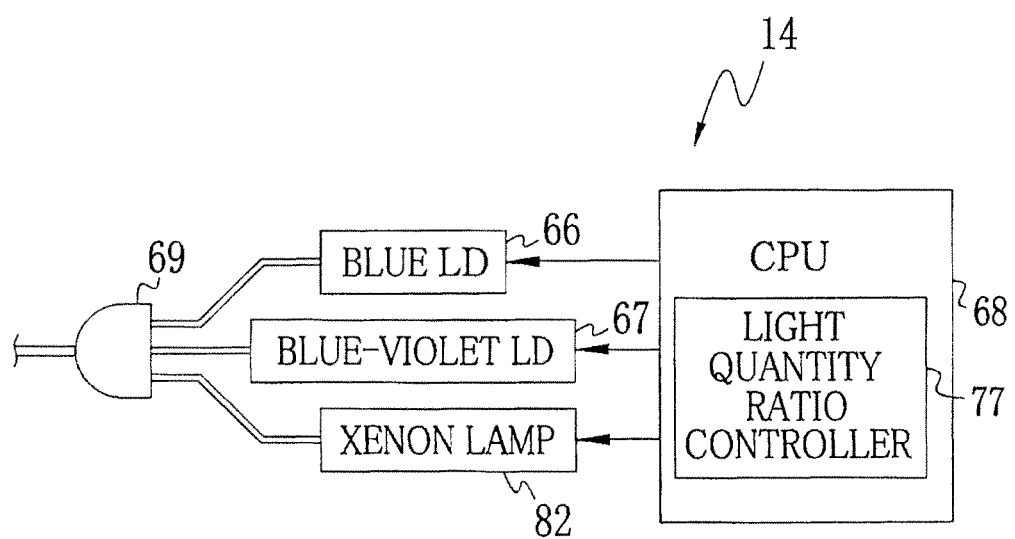
FIG. 20 is a block diagram showing a light source apparatus of further another example.

In this embodiment, the blue-green light is used by way of example. Alternatively or in addition, to suppressor reduce the display of the surface blood vessel 72, light in a different wavelength range may be added as the illumination light to relatively reduce the contrast of the B signal. For example, as shown in FIG. 20, a xenon lamp 82 for emitting white light may be used as a third light source. The xenon lamp 82 is turned on to increase a component of the normal light in the illumination light. Thereby, the contrast of the B signal is reduced relatively to suppress or reduce the display of the surface blood vessel 72.

Third Embodiment

In the first embodiment, the display suppression function to suppress the subsurface blood vessel 73 is described. In the second embodiment, the display suppression function to suppress the surface blood vessel 72 is described. It is preferable that an electronic endoscope system is provided with both of the two display suppression functions. This is because a target blood vessel is selected between the surface blood vessel 72 and the subsurface blood vessel 73 depending on a patient's disease or the like, so it is troublesome and increases patient's burden to exchange the electronic endoscope system depending on whether the target blood vessel is the surface blood vessel 72 or the subsurface blood vessel 73.

Figure 21:
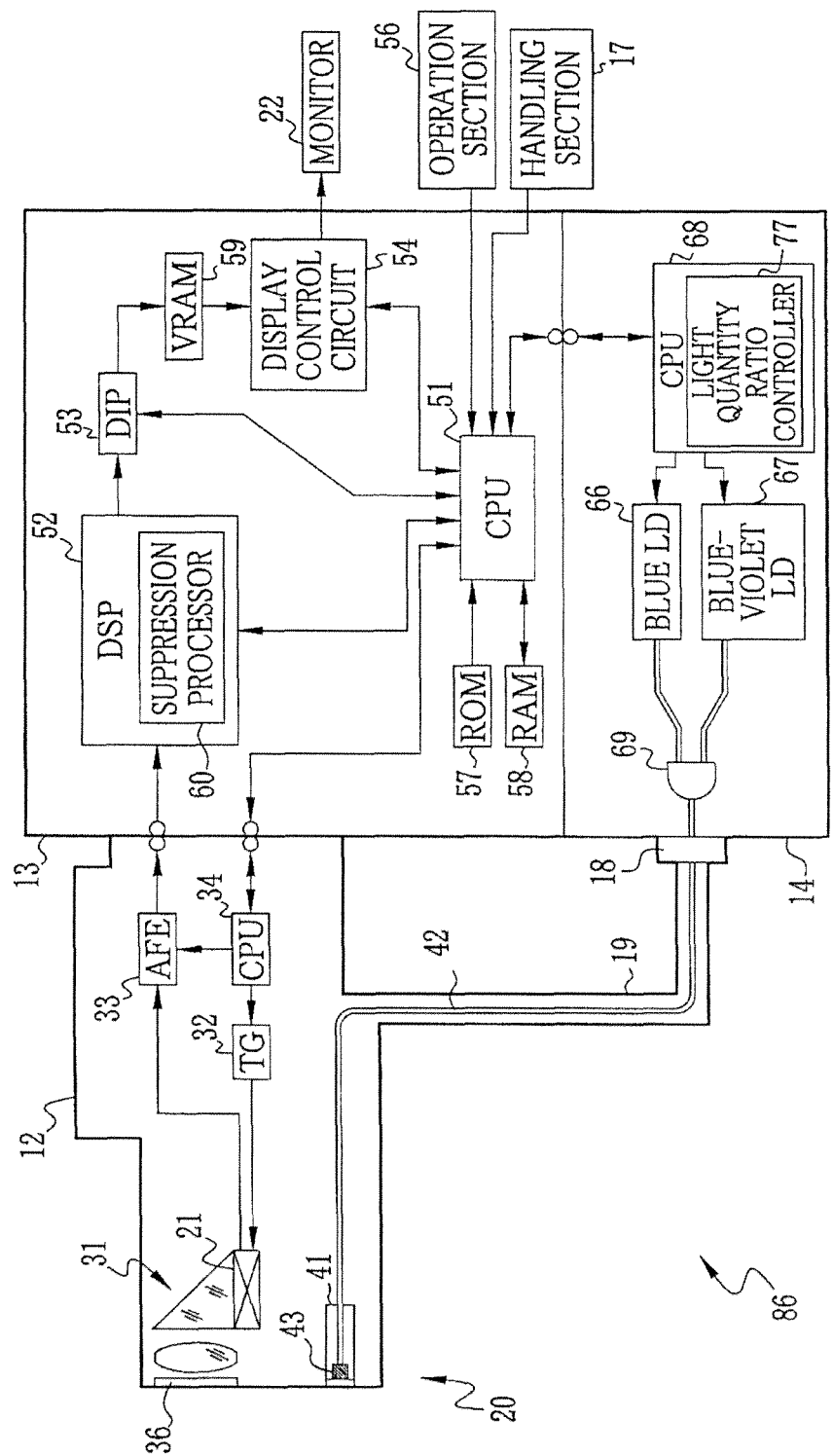
FIG. 21 is a block diagram showing a configuration of an electronic endoscope system of a third embodiment.

Like an electronic endoscope system 86 shown in FIG. 21, to provide the display suppression functions to suppress the displays of the subsurface blood vessel 73 and the surface blood vessel 72 in a single electronic endoscope system, the suppression processor 60 is provided to the DSP 52 and the light quantity ratio controller 77 is provided to the CPU 68 of the light source apparatus 14. One of the suppression processor 60 and the light quantity ratio controller 77 may function according to a display suppression setting.

Figure 22:
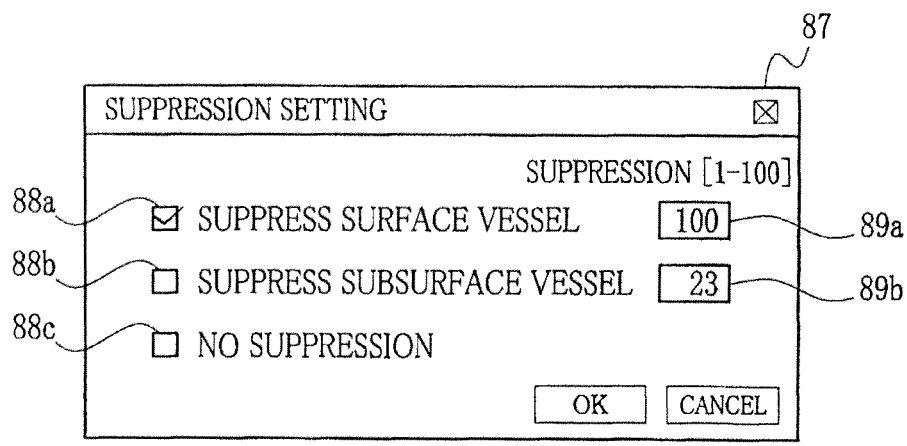
FIG. 22 is an explanatory view showing an example of a GUI used for a display suppression setting.

When both the suppression processor 60 and the light quantity ratio controller 77 are provided to the single electronic endoscope system, it is preferable to use a GUI such as a setting window 87 shown in FIG. 22. The GUI allows a user to set the display suppression setting of the subsurface blood vessel 73 or the surface blood vessel 72 at a time. The setting window 87 is displayed on the monitor 22 by operating the operation section 56. The setting window 87 has alternative checkboxes 88*a* to 88*c* and boxes 89*a* and 89*b* for setting the suppression degree.

To suppress or reduce the display of the surface blood vessel 72, the checkbox 88*a* on the setting window 87 is checked. The suppression degree is set in the box 89*a*. Thereby, the light quantity ratio controller 77 suppresses or reduces the display of the surface blood vessel 72 in accordance with the suppression degree set in the box 89*a*.

To suppress or reduce the display of the subsurface blood vessel 73, the checkbox 88*b* on the setting window 87 is checked. The suppression degree is set in the box 89*b*. Thereby, the suppression processor 60 suppresses or reduces the display of the subsurface blood vessel 73 in accordance with the suppression degree set in the box 89*b*.

When neither the surface blood vessel 72 nor the subsurface blood vessel 73 is suppressed, the checkbox 88*c* is checked. Thereby, the electronic endoscope system 86 activates neither the suppression processor 60 nor the light quantity ratio controller 77. In this case, as described in the first and second embodiments, the electronic endoscope system 86 generates the special light image data 71 during the special light observation.

Note that the setting window 87 is described by way of example. The setting window 87 in a different configuration may be used instead. In the above-described setting window 87, for example, a numerical value is inputted in the box 89*a* or 89*b*. Alternatively, it is preferable to use a slide bar or the like to allow for intuitive operation. Because the setting on the setting window 87 varies with a doctor using the electronic endoscope system, it is preferable to store the setting on a doctor by doctor basis. It is preferable to restore the setting when a doctor inputs his or her ID, for example.

In this embodiment, one of the suppression processor 60 and the light quantity ratio controller 77 is activated to suppress or reduce the display of the subsurface blood vessel 73 or the surface blood vessel 72. To suppress or reduce the display of the surface blood vessel 72, it is also possible to use both the suppression processor 60 and the light quantity ratio controller 77 at a time. This is because the suppression processor 60 can suppress the display of the surface blood vessel 72 by adding the R signal or the G signal to the B signal as described above.

Fourth Embodiment

In the first to third embodiments, out of the surface blood vessel 72 and the subsurface blood vessel 73, the visibility of the target blood vessel is improved by suppressing or reducing the display of the non-target blood vessel regardless of whether the frequency enhancement processing is performed in the DIP 53 by way of example. Alternatively, the frequency enhancement processing in the DIP 53 may be performed in conjunction with the display suppression described in the first to third embodiments. Hereinafter, the single electronic endoscope system 86 is provided with both the suppression processor 60 and the light quantity ratio controller 77 as described in the third embodiment.

Figure 23:
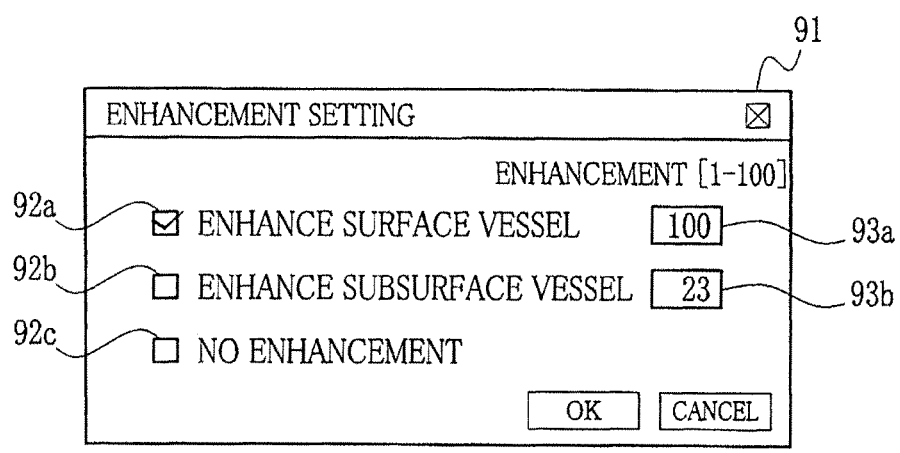
FIG. 23 is an explanatory view showing an example of a GUI used for an enhancement setting.

In this case, as shown in FIG. 23, for example, a setting window 91 is used to select whether the enhancement processing is performed to the surface blood vessel 72 or the subsurface blood vessel 73, or not performed at all. The setting window 91 has alternative checkboxes 92*a* to 92*c* to select the blood vessel to be enhanced or not to perform the enhancement processing. Enhancement degree or the extent of the enhancement of the surface blood vessel 72 is set in a box 93*a*. The enhancement degree of the subsurface blood vessel 73 is set in a box 93*b*. The enhancement degree is set using a numerical value from 1 to 100, for example.

When the checkbox 92*a* is checked to enhance the surface blood vessel 72, the electronic endoscope system operates as follows. The checkbox 92*a* is used for the setting for enhancing the surface blood vessel 72. The checkbox 92*a* is not for selecting the display suppression of the subsurface blood vessel 73. However, the superposition of the surface blood vessel 72, being the target blood vessel, on the subsurface blood vessel 73 hinders the observation, so the CPU 51 of the processor apparatus 13 activates the suppression processor 60 in response to the setting of the frequency enhancement processing to enhance the surface blood vessel 72 set by checking the checkbox 92*a*. With the use of the suppression processor 60, the DSP 52 generates the subsurface vessel suppressed image data 74 based on the imaging signals of respective colors inputted from the CCD 21, and inputs the subsurface vessel suppressed image data 74 to the DIP 53.

The DIP 53 performs the frequency enhancement processing of the predetermined frequency to the subsurface vessel suppressed image data 74, inputted from the DSP 52, so as to enhance the surface blood vessel 72. Only by setting the enhancement setting on the setting window 91, the surface blood vessel 72 is enhanced by the frequency enhancement processing while the display of the subsurface blood vessel 73 is automatically suppressed in the observation image displayed on the monitor 22.

Note that the DIP 53 enhances the image of the surface blood vessel 72 through the frequency enhancement processing in accordance with the enhancement degree inputted to the box 93*a*. When the subsurface vessel suppressed image data 74 is generated, the suppression processor 60, on the other hand, automatically sets the suppression degree to a value (for example, the same value as the enhancement degree) corresponding to the enhancement degree inputted to the box 93*a*. Based on this suppression degree, the addition rate of the R signal is determined.

Similarly, when the checkbox 92*b* is checked to enhance the subsurface blood vessel 73, the electronic endoscope system operates as follows. The checkbox 92*b* is used for the setting for enhancing the subsurface blood vessel 73. The checkbox 92*b* is not for selecting the display suppression of the surface blood vessel 72. However, the surface blood vessel 72 superposed on the subsurface blood vessel 73, being the target blood vessel, hinders the observation, so the CPU 51 of the processor apparatus 13 activates the light quantity ratio controller 77 in response to the setting of the frequency enhancement processing to enhance the subsurface blood vessel 73 set by checking the checkbox 92*b*. To enhance the subsurface blood vessel 73, the light quantity ratio controller 77 controls the light quantity ratio between the blue LD 66 and the blue-violet LD 67 to control a component in the illumination light. Thereby, the DSP 52 generates the special light image data 71, being the surface vessel suppressed image data 78.

The DIP 53 performs the frequency enhancement processing of the predetermined frequency to the surface vessel suppressed image data 78, inputted from the DSP 52, so as to enhance the subsurface blood vessel 73. Only by setting the enhancement setting on the setting window 91, the subsurface blood vessel 73 is enhanced by the frequency enhancement processing while the display of the surface blood vessel 72 is automatically suppressed in the observation image displayed on the monitor 22.

Note that the DIP 53 enhances the image of the subsurface blood vessel 73 through the frequency enhancement processing in accordance with the enhancement degree inputted to the box 93b. On the other hand, when the light quantity ratio controller 77 controls the light quantity ratio between the blue LD 66 and the blue-violet LD 67, the suppression degree of the image of the surface blood vessel 72 is automatically set to a value (for example, the same value as the enhancement degree) corresponding to the enhancement degree inputted to the box 93b. Based on the suppression degree, the light quantity ratio controller 77 determines the light quantity ratio between the blue LD 66 and the blue-violet LD 67.

When the enhancement processing by the DIP 53 is performed in conjunction with the display suppression, the display of fine tissue which hinders the observation is automatically suppressed or reduced only by selecting a target portion to be observed. There is no need to set the enhancement and the suppression separately. Thus, the usability improves.

In the fourth embodiment, the display of the non-target blood vessel is suppressed or reduced in response to the setting of the enhancement processing of the target blood vessel by way of example. Conversely, the enhancement processing may be performed automatically in response to the display suppression setting. In this case, the blood vessel not selected for the display suppression is determined as the target blood vessel.

In the fourth embodiment, the single electronic endoscope system provided with both the suppression processor 60 and the light quantity ratio controller 77 is described by way of example. The setting for the enhancement processing and the setting for display suppression may work together also in the electronic endoscope system 11 of the first embodiment or the electronic endoscope system 76 of the second embodiment.

Fifth Embodiment

In the first to fourth embodiments, the so-called synchronous electronic endoscope system for capturing color images is described by way of example. Alternatively, for example, an electronic endoscope system of the so-called frame sequential method can also suppress or reduce the display of the surface blood vessel 72 or the subsurface blood vessel 73. The electronic endoscope system of the frame sequential method uses a monochrome image sensor. Each image is captured for each color, sequentially. Images of respective colors are combined to obtain a color image. Hereinafter, an example of the electronic endoscope of the frame sequential method is described. Parts similar to those in the first to fourth embodiments are designated with similar reference numerals and descriptions thereof are omitted.

Figure 24:
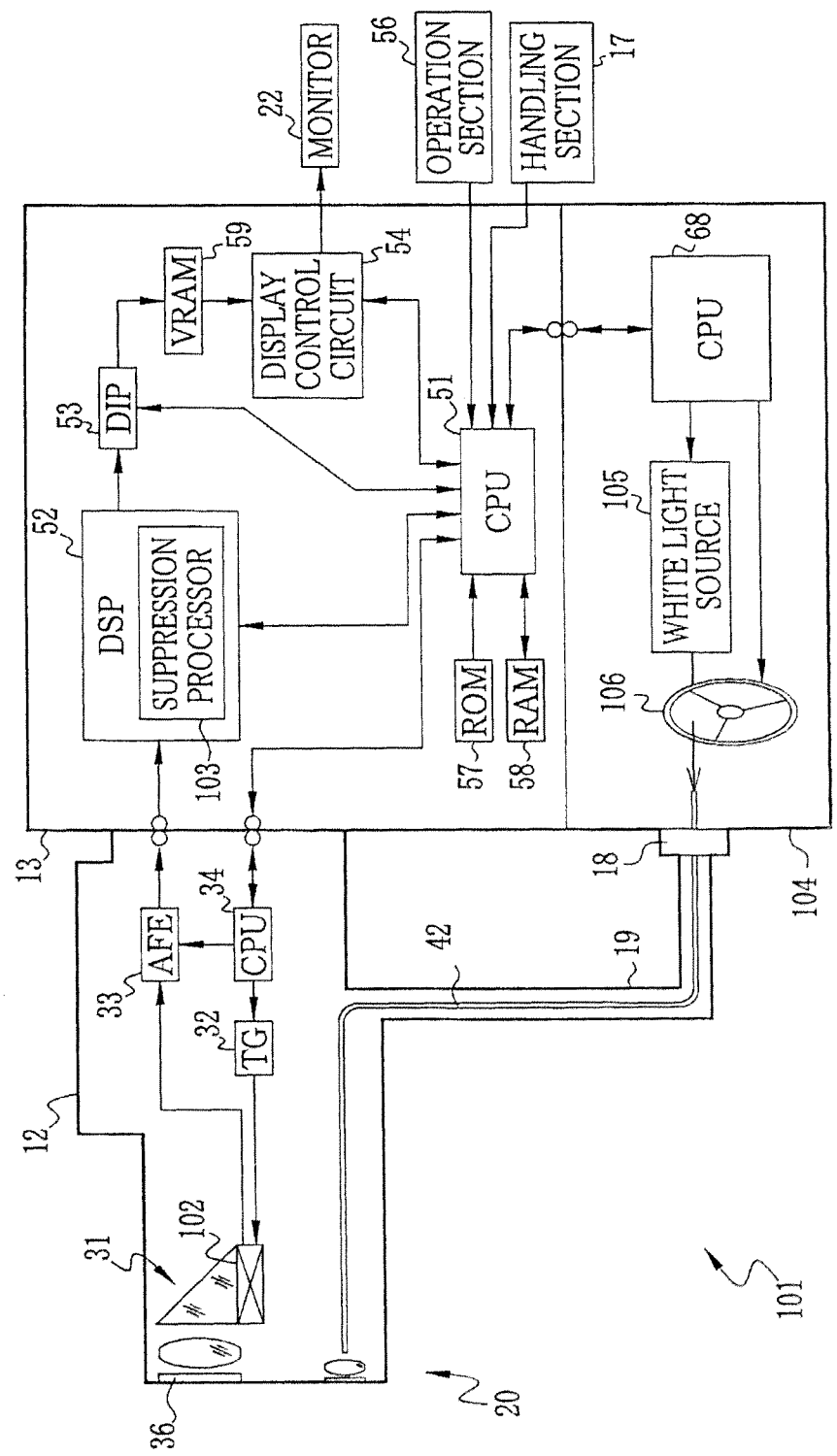
FIG. 24 is a block diagram showing a configuration of an electronic endoscope system of a fifth embodiment.

As shown in FIG. 24, in an electronic endoscope system 101, the electronic endoscope 12 is provided with a CCD 102 being an image sensor. The CCD 102 is a monochrome image sensor with no color filter. An image is captured very time illumination light of a different color is applied to the target portion.

The DSP 52 generates image data of a single frame based on imaging signals of multiple frames outputted from the CCD 102. According to a setting, the DSP 52 combines the R, G, and B signals to generate the normal light image data. The DSP 52 combines, for example, a blue image captured under the blue illumination light and a green image captured under the green illumination light to generate image data, which will be described later, corresponding to the special light image data 71.

The DSP 52 is provided with a suppression processor 103. Based on the imaging signals of respective colors inputted sequentially from the CCD 102, the suppression processor 103 generates image data in which the display of the surface blood vessel 72 or the subsurface blood vessel 73 is suppressed or reduced. The suppression processor 103 operates to suppress or reduce the display of the surface blood vessel 72 or the subsurface blood vessel 73.

A light source apparatus 104 is provided with a white light source 105 and a rotation filter 106. The white light source 105 is a white LD, an LED, or a xenon lamp, for example, and emits broadband white light. The CPU 68 controls emission timing and quantity of light emitted from the white light source 105.

The rotation filter 106 is disposed in front of the white light source 105. The rotation filter 106 filters narrowband light of a predetermined wavelength range out of the white light emitted from the white light source 105, and allows the narrowband light to be incident on the electronic endoscope 12. The rotation filter 106 is composed of multiple sections (filters), which will be described later. Each section allows the narrowband light of a different wavelength range to pass therethrough. The rotation filter 106 is disposed in a rotatable manner. The CPU 68 controls to rotate the rotation filter 106 at predetermined timing. Thereby, the wavelength range of the narrowband light, being the illumination light, to be applied to the target portion is changed sequentially.

After passing through the rotation filter 106, the narrowband light, being the illumination light, is guided to the light guide 42 through a lens or the like (not shown). The narrowband light is applied to the target portion through a lens, a capture window, and the like (not shown) provided in the distal portion 20 of the electronic endoscope 12.

Figure 25:
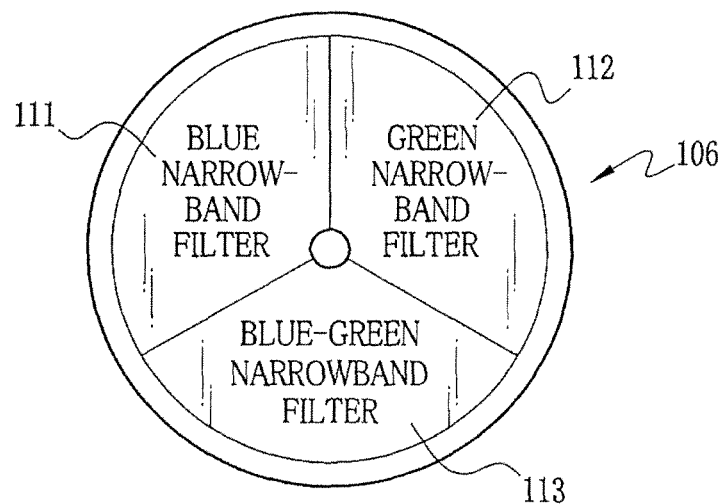
FIG. 25 is an explanatory view showing a configuration a rotation filter.

As shown in FIG. 25, the rotation filter 106 is provided with three kinds of filters each passing light (hereinafter referred to as the narrowband light) in a narrow wavelength range. A blue narrowband filter 111 passes blue narrowband light. A green narrowband filter 112 passes green narrowband light. A blue-green narrowband filter 113 passes blue-green narrowband light. For example, the blue narrowband light has a wavelength of 415 nm. The green narrowband light has a wavelength of 540 nm. The blue-green narrowband light has a wavelength of 445 nm. For the sake of easy explanation, the rotation filter 106 is composed of three sections (filters) with the equal size: the blue narrowband filter 111, the green narrowband filter 112, and the blue-green narrowband filter 113. Alternatively or in addition, for example, a filter passing narrowband light of a different color, for example, red, a filter passing light of a specific wavelength range, or a filter for passing/blocking the light of all colors may be used. An angle of each filter may be determined in accordance with the emission time of each narrowband light.

Figure 26:
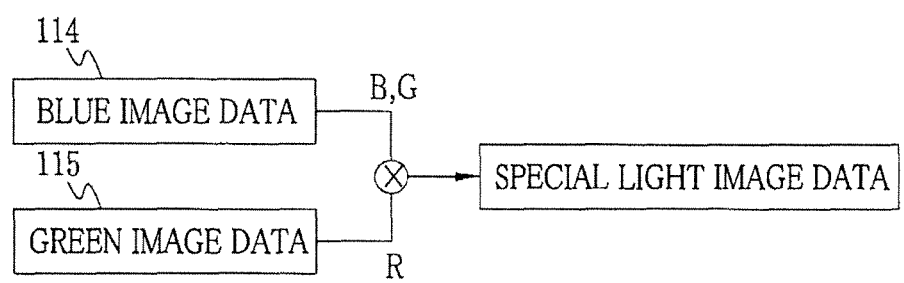
FIG. 26 is an explanatory view showing generation of the special light image data.

As shown in FIG. 26, to perform the special light observation using the electronic endoscope system 101, the DSP 52 generates blue image data 114 based on a blue signal obtained under the illumination of the blue narrowband light passed through the blue narrowband filter 111. The DSP 52 generates green image data 115 based on a green signal obtained under the illumination of the green narrowband light passed through the green narrowband filter 112. Then, the DSP 52 generates image data in which the blue image data 114 is assigned to the B and G pixels and the green image data 115 is assigned to the R pixel. This image data corresponds to the special light image data 71 described in the first to fourth embodiments.

To suppress or reduce the display of the subsurface blood vessel 73, the DSP 52 generates blue-green image data 116 based on a blue-green signal obtained under the illumination of the blue-green narrowband light passed through the blue-green narrowband filter 113, in addition to the blue and green image data 114 and 115. Then, the DSP 52 generates subsurface vessel suppressed image data 117 with the use of the suppression processor 103.

Figure 27:
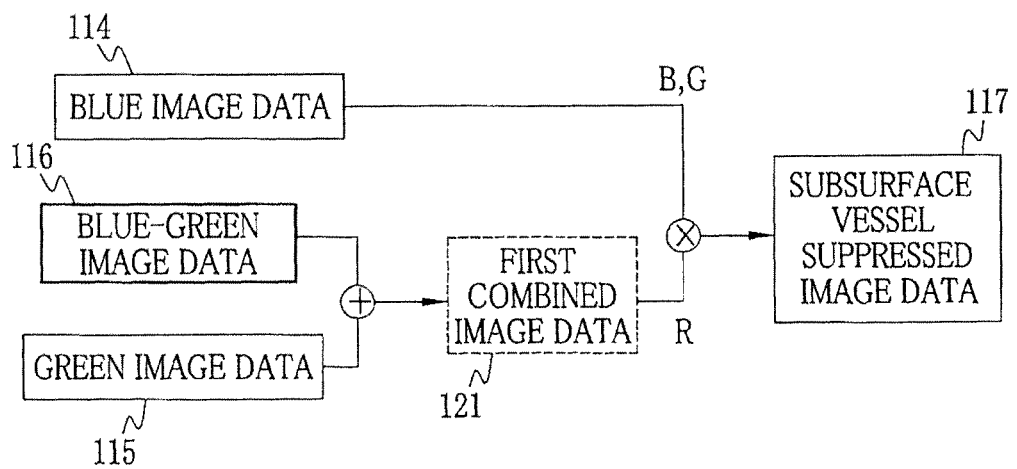
FIG. 27 is an explanatory view showing generation of the subsurface vessel suppressed image data.

As shown in FIG. 27, to generate the subsurface vessel suppressed image data 117, first, the suppression processor 103 generates first combined image data 121. The first combined image data 121 is generated by adding the green image data 115 and the blue-green image data 116 on a pixel by pixel basis. The contrast of the subsurface blood vessel 73 is shown in the green image data 115. When compared with light of other wavelength, there are small differences in reflectance among the surface blood vessel 72, the subsurface blood vessel 73, and the mucosa at the blue-green narrowband light (445 nm) (see FIG. 19). Accordingly, the subsurface blood vessel 73 and the surface blood vessel 72 show low contrast in the blue-green image data 116. By adding the blue-green image data 116 and the green image data 115, the contrast of the subsurface blood vessel 73 in the first combined image data 121 is reduced relative to that in the green image data 115.

In generating the first combined image data 121, the blue-green image data 116 is added to the green image data 115 with weighting determined by the suppression degree. For example, a proportion of the blue-green image data 116 increases relative to the green image data 115 as the suppression degree increases. Thereby, the contrast of the subsurface blood vessel 73 is further reduced.

The suppression processor 103 uses the first combined image data 121 for the R pixel and the blue image data 114 for the B and G pixels to combine the first combined image data 121 and the blue image data 114. Thereby, the subsurface vessel suppressed image data 117 is generated. The contrast of the surface blood vessel 72 is shown in the blue image data 114. Accordingly, the contrast of the subsurface vessel suppressed image data 117, being the image of the B and G pixels, generated by the suppression processor 103 is similar to that in the blue image data 114. On the other hand, the contrast of the subsurface blood vessel 73 is reduced when the first combined image data 121 is generated. Accordingly, the contrast of the subsurface blood vessel 73 is low and thus the display thereof is suppressed or reduced in the subsurface vessel suppressed image data 117.

To suppress or reduce the display of the surface blood vessel 72, the DSP 52 generates the blue image data 114, the green image data 115, and the blue-green image data 116. Then, the DSP 52 generates surface vessel suppressed image data 118 with the use of the suppression processor 103.

Figure 28:
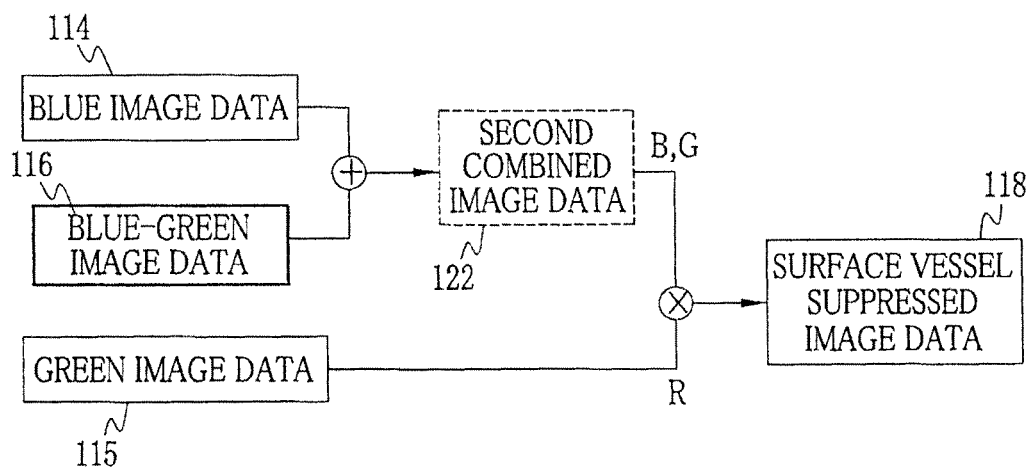
FIG. 28 is an explanatory view showing generation of the surface vessel suppressed image data.

To generate the surface vessel suppressed image data 118, as shown in FIG. 28, first, the suppression processor 103 adds the blue-green image data 116 to the blue image data 114 on a pixel by pixel basis to generate second combined image data 122. The contrast of the surface blood vessel 72 is shown in the blue image data 114. As described above, there are small differences in reflectance among the surface blood vessel 72, the subsurface blood vessel 73, and the mucosa at the wavelength of the blue-green narrowband light, so the surface blood vessel 72 shows low contrast in the blue-green image data 116. Accordingly, by adding the blue-green image data 116 to the blue image data 114, the contrast of the surface blood vessel 72 in the second combined image data 122 is reduced relative to that in the blue image data 114.

In generating the second combined image data 122, the blue-green image data 116 is added to the blue image data 114 with weighting determined by the suppression degree. For example, a proportion of the blue-green image data 116 increases relative to the blue image data 114 as the suppression degree increases. Thereby, the contrast of the surface blood vessel 72 is further reduced.

The suppression processor 103 uses the second combined image data 122 for the B and G pixels. The green image data 115 is used for the R pixel. The suppression processor 103 combines the second combined image data 122 and the blue image data 114 to generate the surface vessel suppressed image data 118. The contrast of the subsurface blood vessel 73 is shown in the green image data 115. Accordingly, the contrast of the subsurface blood vessel 73, being the image of the R pixel, is similar to that of green image data 115 in the surface vessel suppressed image data 118. On the other hand, because the contrast of the surface blood vessel 72 is reduced when the second combined image data 122 is generated, the contrast of the surface blood vessel 72 is low in the surface vessel suppressed image data 118. Thus, the display of the surface blood vessel 72 is suppressed.

Figure 29:
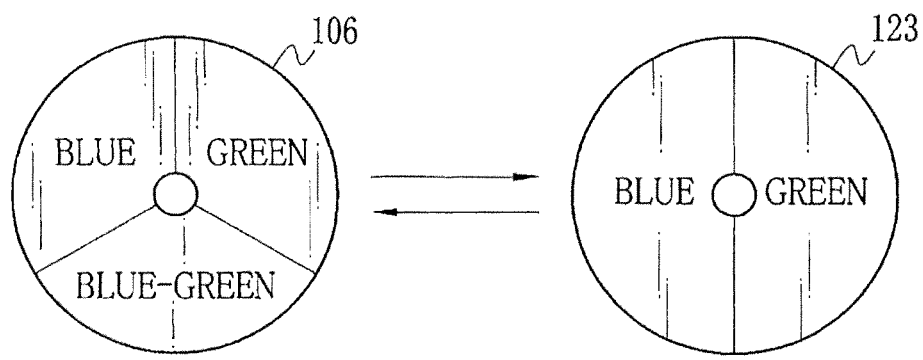
FIG. 29 is an explanatory view of an example of an exchangeable rotation filter.

Alternatively or in addition to the rotation filter 106, another filter may be used. For example, as shown in FIG. 29, a rotation filter 123 may be provided in addition to the rotation filter 106 in an exchangeable manner. The rotation filter 123 is provided with the blue narrowband filter 111 and the green narrowband filter 112. To suppress or reduce the display of the surface blood vessel 72 or the subsurface blood vessel 73, the rotation filter 106 is used. When the display of neither the surface nor subsurface blood vessels 72 and 73 are suppressed, the rotation filter 123 may be used.

Figure 30:
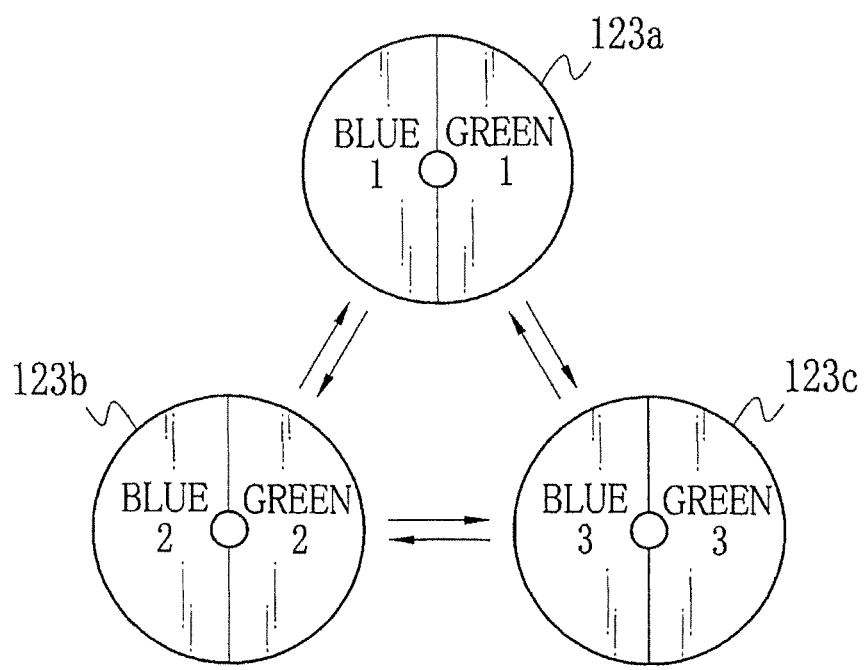
FIG. 30 is an explanatory view of another example of the exchangeable rotation filter.

For example, as shown in FIG. 30, the rotation filters 123a to 123c may be provided in an exchangeable manner. Each of the rotation filters 123a to 123c is provided with two kinds of filters, a blue narrowband filter and a green narrowband filter. All of the blue narrowband filters (Blue 1 to Blue 3) of the rotation filters 123a to 123c pass the blue narrowband light, but differ from each other in transmission wavelength range. Accordingly, each of the rotation filters 123a to 123c provides different contrast of the surface blood vessel 72 in the blue image data 114.

Similarly, all of the green narrowband filters (Green 1 to Green 3) of the rotation filters 123a to 123c pass green narrowband light. However, the green narrowband filters (Green 1 to Green 3) differ from each other in transmission wavelength. Accordingly, each of the rotation filters 123a to 123c provides different contrast of the subsurface blood vessel 73 in the green image data 115.

A suitable filter is selected among the rotation filters 123a to 123c depending on which of the surface blood vessel 72 and the subsurface blood vessel 73 is to be suppressed and the set suppression degree. Thereby image data in which the display of the surface blood vessel 72 or the subsurface blood vessel 73 is suppressed is obtained. When the blue image data 114 and the green image data 115, obtained with the use of one of the rotation filters 123a to 123c, are combined in a manner described in FIG. 26, the special light image data with no display suppression, the subsurface vessel suppressed image data 117, or the surface vessel suppressed image data 118 is obtained according to the filter used.

Note that in the electronic endoscope system 101 of the fifth embodiment, the subsurface vessel suppressed image data 117, generated by adding the blue-green image data 116 to the green image data 115, and the surface vessel suppressed image data 118, generated by adding the blue-green image data 116 to the blue image data 114, change their respective color tones relative to the image with no display suppression, similar to the first to fourth embodiments. Accordingly, it is preferable to correct the color tone of each of the image data 114 and 115 through the gain correction and the color tone correction as described in the first and second embodiments. The color tone may be corrected by multiplying each of the blue-green image data 116 and the green image data 115 (or the blue image data 114) by a predetermined coefficient so as to make the total pixel value constant when the blue-green image data 116 is added to the green image data 115 (or the blue image data 114), as described in the first and second embodiments.

In the fifth embodiment, the display of the surface blood vessel 72 or that of the subsurface blood vessel 73 is suppressed by way of example. Alternatively, as described in the fourth embodiment, the display suppression may be performed in conjunction with the display enhancement.

In the fifth embodiment, the blue-green narrowband filter 113 is provided. The blue-green image data 116, obtained when the blue-green light is used as the illumination light, is added to the blue image data 114 to suppress or reduce the display of the surface blood vessel 72 or to the green image data 115 to suppress or reduce the display of the subsurface blood vessel 73 by way of example. For the display suppression, any image data in which the contrast of the surface blood vessel 72 or the subsurface blood vessel 73 is low may be added to the blue image data 114 or to the green image data 115. For example, red image data obtained under illumination of red narrowband light, or white light image data obtained under illumination of the white light may be added. The rotation filter 106 is provided with a necessary filter, an opening and the like.

In the first to fourth embodiments, the image data is generated by assigning the B signal outputted from the CCD 21 to the B and G pixels and by assigning the G signal to the R pixel by way of example. In the fifth embodiment, the image data is generated by assigning the blue image data 114 to the B and G pixels and by assigning the green image data 115 to the R pixel by way of example. Alternatively, the display of the surface blood vessel 72 or the subsurface blood vessel 73 may be suppressed by assigning the B signal to the B pixel, the G signal to the G pixel, and the R signal to the R pixel in a manner similar to the first and fourth embodiments. The display of the surface blood vessel 72 or the subsurface blood vessel 73 may be suppressed similarly in the electronic endoscope system 101 of the frame sequential method.

In the first to fifth embodiments, the CCD is used as the image sensor by way of example. Alternatively, a CMOS or the like may be used as the image sensor. The number, arrangement, and the like of the image sensor(s) may be changed as necessary.

In the first to fifth embodiments, the DSP 52 is provided with the suppression processor. The display of the non-target blood vessel is suppressed through signal processing of the image data by way of example. Alternatively, for example, the DSP 52 may generate image data on a color by color basis based on the imaging signal inputted from the CCD. The image data of respective colors are combined in the DIP 53. Thereby, an observation image, similar to that described in first to fifth embodiments, in which the display of the non-target blood vessel is suppressed is generated.

Various changes and modifications are possible in the present invention and may be understood to be within the present invention.

What is claimed is:

1. An electronic endoscope system comprising:
   an illumination section for applying illumination light to a portion to be observed inside a body, the portion including a surface blood vessel and a subsurface blood vessel located deeper than the surface blood vessel, the illumination light including blue light and green light, light absorption by the surface blood vessel being larger in a wavelength range of the blue light, light absorption by the subsurface blood vessel being larger in a wavelength range of the green light;
   an imaging section for capturing reflection light reflected from the portion, having a color image sensor which outputs a blue imaging signal corresponding to the blue light, a green imaging signal corresponding to the green light, and a red imaging signal corresponding to red light that is a smaller quantity of light absorbed by hemoglobin compared to the blue and green light, the color image sensor having color filters respectively corresponding to the blue, green, and red lights on each pixel;
   a suppression section for reducing contrast of the subsurface blood vessel in the green imaging signal by adding the red imaging signal to the green imaging signal; and
   an image generating section for generating an image based on at least the green imaging signal to which the red imaging signal is added and the blue imaging signal.

2. The electronic endoscope system of claim 1, wherein the suppression section changes an addition rate of the red imaging signal to the green imaging signal.

3. The electronic endoscope system of claim 1, wherein the image generating section assigns the blue imaging signal to B pixel and G pixel in the image and assigns the green imaging signal to which the red imaging signal is added to R pixel in the image.

4. The electronic endoscope system of claim 1, further including an enhancement processing section for performing enhancement processing to enhance the surface blood vessel relative to the subsurface blood vessel.

5. The electronic endoscope system of claim 4, wherein the suppression section reduces contrast of the subsurface blood vessel in the green imaging signal in conjunction with the enhancement processing performed by the enhancement processing section.

6. The electronic endoscope system of claim 1, further including a color tone corrector for correcting a color tone of the image.

7. An electronic endoscope system, comprising:
   an illumination section for applying illumination light to a portion to be observed inside a body, the portion including a surface blood vessel and a subsurface blood vessel located deeper than the surface blood vessel, the illumination light including blue light and green light, light absorption by the surface blood vessel being larger in a wavelength range of the blue light, light absorption by the subsurface blood vessel being larger in a wavelength range of the green light;
   an imaging section for capturing reflection light reflected from the portion, having a color image sensor which outputs a blue imaging signal corresponding to the blue light, a green imaging signal corresponding to the green light, and a red imaging signal corresponding to red light that is a small quantity of light absorbed by hemoglobin compared to the blue and green light, the color image sensor having color filters respectively corresponding to the blue, green and red lights on each pixel;

a suppression section for reducing contrast of the surface blood vessel in the blue imaging signal by adding the red imaging signal to the blue imaging signal; and
an image generating section for generating an image based on at least the blue imaging signal to which the red imaging signal is added and the green imaging signal.

* * * * *